US010448875B2

(12) United States Patent
Holt et al.

(10) Patent No.: US 10,448,875 B2
(45) Date of Patent: Oct. 22, 2019

(54) CAPACITIVE MEASUREMENT DEVICE WITH INTEGRATED ELECTRICAL AND MECHANICAL SHIELDING

(71) Applicants: Stream Dx, Inc, West Valley City, UT (US); University of Utah Research Foundation, Salt Lake City, UT (US)

(72) Inventors: Brian D. Holt, North Salt Lake, UT (US); Scott B. McClellan, Park City, UT (US); Alvin Y. Le, Salt Lake City, UT (US); Kent James Ogden, Midvale, UT (US)

(73) Assignees: Stream Dx, Inc, West Valley City, UT (US); University of Utah Research Foundation, Salt Lake City, UT (US)

( * ) Notice: Subject to any disclaimer, the term of this patent is extended or adjusted under 35 U.S.C. 154(b) by 754 days.

(21) Appl. No.: 14/884,591

(22) Filed: Oct. 15, 2015

(65) Prior Publication Data

US 2017/0105670 A1 Apr. 20, 2017

(51) Int. Cl.

*A61B 5/20* (2006.01)
*A61B 5/00* (2006.01)
*G01F 1/56* (2006.01)

(52) U.S. Cl.

CPC ............ *A61B 5/208* (2013.01); *A61B 5/0002* (2013.01); *G01F 1/56* (2013.01); (Continued)

(58) Field of Classification Search

CPC .......... A61F 5/451; A61F 5/455; A61F 5/453; A61B 5/208; A61B 10/007

See application file for complete search history.

(56) References Cited

U.S. PATENT DOCUMENTS 4,051,431 A 9/1977 Wurster
4,628,612 A 12/1986 Hori et al.

(Continued)

FOREIGN PATENT DOCUMENTS

RU 2026639 1/1995
RU 2034516 5/1995

(Continued)

OTHER PUBLICATIONS

International Search Authority, "Notice of International Search Report and Written Opinion for PCT/US16/56877", "Foreign Counterpart of U.S. Appl. No. 14/884,591", dated Jan. 12, 2017, pp. 1-10, Published in: WO.

(Continued)

*Primary Examiner* — Patrick Fernandes
(74) *Attorney, Agent, or Firm* — Fogg & Powers LLC

(57) ABSTRACT

A substance measurement device includes: a container portion configured to receive a substance; a sensing device configured to measure a property of the substance related to at least one of a flow rate of the substance into the container portion, a level of the substance within the container portion, and a volume of the substance within the container portion; and at least one shield positioned within the container portion and configured to provide at least one of: a mechanical buffer between the substance entering the container portion and the sensing device; and an electrical shield between the substance entering the container portion and the sensing device.

26 Claims, 31 Drawing Sheets

(52) U.S. Cl.
CPC ................. *A61B 2560/0223* (2013.01); *A61B 2560/0252* (2013.01); *A61B 2562/227* (2013.01)

(56) References Cited

U.S. PATENT DOCUMENTS

| | | | | |
|---|---|---|---|---|
| 5,311,769 | A | 5/1994 | Hetzel | |
| 5,423,206 | A | 6/1995 | Hetzel | |
| 5,672,831 | A | 9/1997 | Codina et al. | |
| 5,726,908 | A | 3/1998 | Hosmer et al. | |
| 5,769,087 | A | 6/1998 | Westphal et al. | |
| 6,125,696 | A | 10/2000 | Hannan et al. | |
| 6,490,920 | B1 | 12/2002 | Netzer | |
| 7,188,426 | B2 | 3/2007 | Barr | |
| 7,258,005 | B2 | 8/2007 | Nyce | |
| 7,360,424 | B2 | 4/2008 | Urano et al. | |
| 7,483,805 | B2 | 1/2009 | Sparks et al. | |
| 7,611,500 | B1 | 11/2009 | Lina et al. | |
| 7,691,092 | B2 | 4/2010 | Corcos et al. | |
| 7,722,584 | B2 | 5/2010 | Tanaka et al. | |
| 7,845,224 | B2 | 12/2010 | Barlesi et al. | |
| 8,116,993 | B2 | 2/2012 | Cebulski | |
| 8,337,476 | B2 | 12/2012 | Greenwald et al. | |
| 8,549,764 | B2 | 10/2013 | Muyskens et al. | |
| 8,924,005 | B2 | 12/2014 | Kern | |
| 8,986,613 | B2 | 3/2015 | Cohen | |
| 2008/0081000 | A1* | 4/2008 | MacLeod | G01M 3/329 422/68.1 |
| 2009/0031790 | A1* | 2/2009 | Guo | A61B 10/007 73/64.56 |
| 2011/0083504 | A1 | 4/2011 | Unger | |
| 2012/0123233 | A1* | 5/2012 | Cohen | A61B 10/007 600/345 |
| 2015/0105694 | A1 | 4/2015 | Mahajan | |

FOREIGN PATENT DOCUMENTS

| | | |
|---|---|---|
| RU | 2256884 | 7/2005 |
| WO | 199910714 | 3/1999 |
| WO | 2014141234 | 9/2014 |
| WO | 2014145971 | 9/2014 |
| WO | 2015153470 | 10/2015 |

OTHER PUBLICATIONS

"Projected Capacitive Technology", "Touch Technology Brief", Oct. 2013, pp. 1-8, Publisher: 3M.
Barrett et al., "Projected-Capacitive Touch Technology", "Frontline Technology", Mar. 2010, pp. 16-21, Publisher: Information Display.
Chiang, Cheng-Ta, "A Semicylindrical Capacitive Sensor with Interface Circuit Used for Flow Rate Measurement", "IEEE Sensors Journal", Dec. 6, 2006, pp. 1564-1570, vol. 6, No. 6, Publisher: IEEE.
"CLC Application Note V2", Jul. 29, 2015, pp. 1-3, Publisher: First Sensor.
"Measuring Transition Points in Liquids with Different Densities with CLC and CLW Capacitive Level Sensors", Jul. 2013, pp. 1-3, Publisher: First Sensor.
"CLC Performance Optimization", Sep. 2015, pp. 1-3, Publisher: First Sensor.
"CLC Series Miniature Capacitive Continuous Liquid Level Sensors", Jul. 2015, pp. 1-6, Publisher: First Sensor.
Liu et al., "A New Cylindrical Capacitance Sensor for Measurement of Water Cut in a Low-production Horizontal Well", "Journal of Physics: Conference Series 147; The 6th International Symposium on Measurement Techniques for Multiphase Flows", at least as early as Dec. 2009, pp. 1-7, Publisher: IOP Publishing.
Otero et al., "A New Device to Automate the Monitoring of Critical Patients' Urine Output", "BioMed Research International", Jan. 28, 2014, pp. 1-8, vol. 2014, Publisher: Hindawi Publishing Corporation.
Paillat et al., "'Capacitive Sensor' to Measure Flow Electrification and Prevent Electrostatic Hazards", "Sensors", Oct. 25, 2012, pp. 14315-14326.
Hotaling et al., "PCT Application No. PCT/US2015/023364", "Fluid Analysis Device and Associated Systems and Methods", Mar. 30, 2015, pp. 1-51, Published in: WO.
"Stream DX Poster, Bench to Bedside, University of Utah Health Sciences", Apr. 2015, p. 1 Publisher: Stream DX, Inc.
"Stream Dx About Us Webpage", "http://streamdxmed.com/aboutus/", at least as early as Oct. 13, 2015, pp. 1-4.
"Stream Dx Home Page", "http://streamdxmed.com/", at least as early as Oct. 13, 2015, No. 1-2.

* cited by examiner

CAPACITIVE MEASUREMENT DEVICE WITH INTEGRATED ELECTRICAL AND MECHANICAL SHIELDING

BACKGROUND

Uroflowmetry is the measure of the volume of urine released from the body, the rate at which urine is voided, and the time it takes to complete a voiding event. The results of a uroflowmetry test can be very beneficial in evaluating the health of the urinary tract. This test can also be very valuable in diagnosing abnormal health conditions, such as lower urinary tract symptoms, benign prostatic hypertrophy, prostate cancer, bladder tumor, neurogenic bladder dysfunction, urinary incontinence, urinary blockage, urinary tract infection, as well as other conditions. Traditionally, uroflowmetry tests are conducted at a medical facility, such as a hospital or clinic. Testing in an artificial clinical setting opposed to a natural setting such as the patient's home can have a significant impact on the patient's performance. In addition to the obvious disadvantages of inconvenience and patient compliance, one complication that often arises with in-clinic testing is that the patient will need to urinate while waiting for the test to be administered. This can result in premature voiding or abnormal voiding events, which skew or negate the value of the test and require the patient to return to the clinic multiple times to get accurate results.

SUMMARY

A substance measurement device includes: a container portion configured to receive a substance; a sensing device configured to measure a property of the substance related to at least one of a flow rate of the substance into the container portion, a level of the substance within the container portion, and a volume of the substance within the container portion; and at least one shield positioned within the container portion and configured to provide at least one of: a mechanical buffer between the substance entering the container portion and the sensing device; and an electrical shield between the substance entering the container portion and the sensing device.

DRAWINGS

Understanding that the drawings depict only exemplary embodiments and are not therefore to be considered limiting in scope, the exemplary embodiments will be described with additional specificity and detail through the use of the accompanying drawings, in which.

DETAILED DESCRIPTION

Figure 1A:
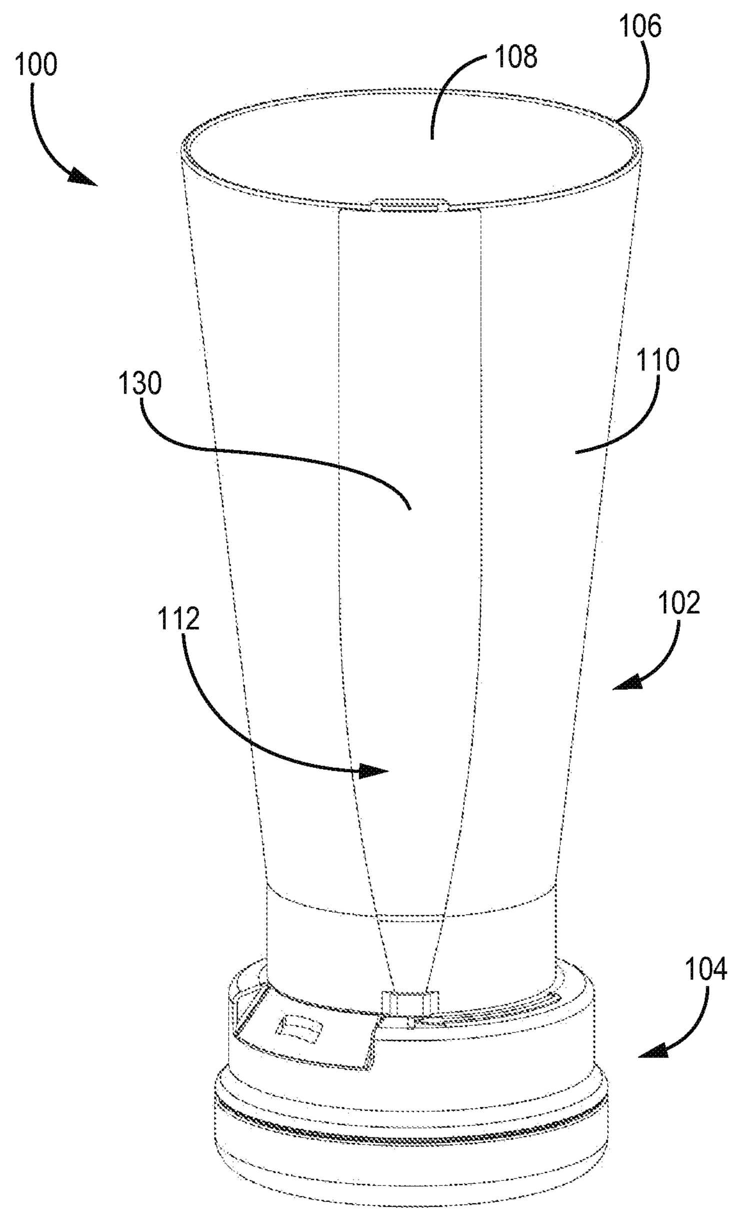
FIG. 1A is a top perspective view of an exemplary embodiment of a urine measurement device, including a container portion and an electronics portion.

In the following detailed description, reference is made to the accompanying drawings that form a part hereof, and in which is shown by way of illustration specific illustrative embodiments. However, it is to be understood that other embodiments may be utilized and that logical, mechanical, and electrical changes may be made. Furthermore, the method presented in the drawing figures and the specification is not to be construed as limiting the order in which the individual steps may be performed. The following detailed description is, therefore, not to be taken in a limiting sense.

In exemplary embodiments, a urine measurement device includes a container portion and an electronics portion that are configured to be connected together. While this description places primary focus on uroflowmetry, it is understood that the description herein can apply more broadly to a substance measurement and/or analysis device that can make measurements about a substance entering into the container portion. In exemplary embodiments, the substance is urine or another bodily fluid, though other liquids, fluids, and/or solids could also be measured.

Figure 1B:
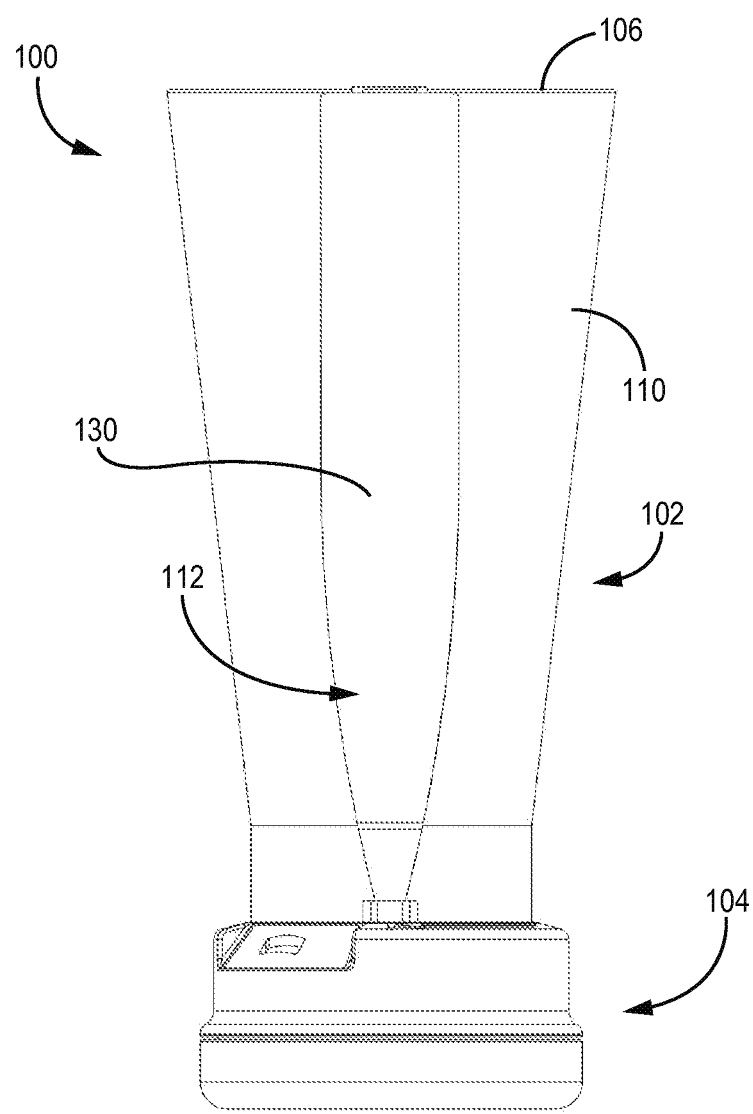
FIG. 1B is a side view of an exemplary embodiment of the urine measurement device of FIG. 1A.
Figure 1C:
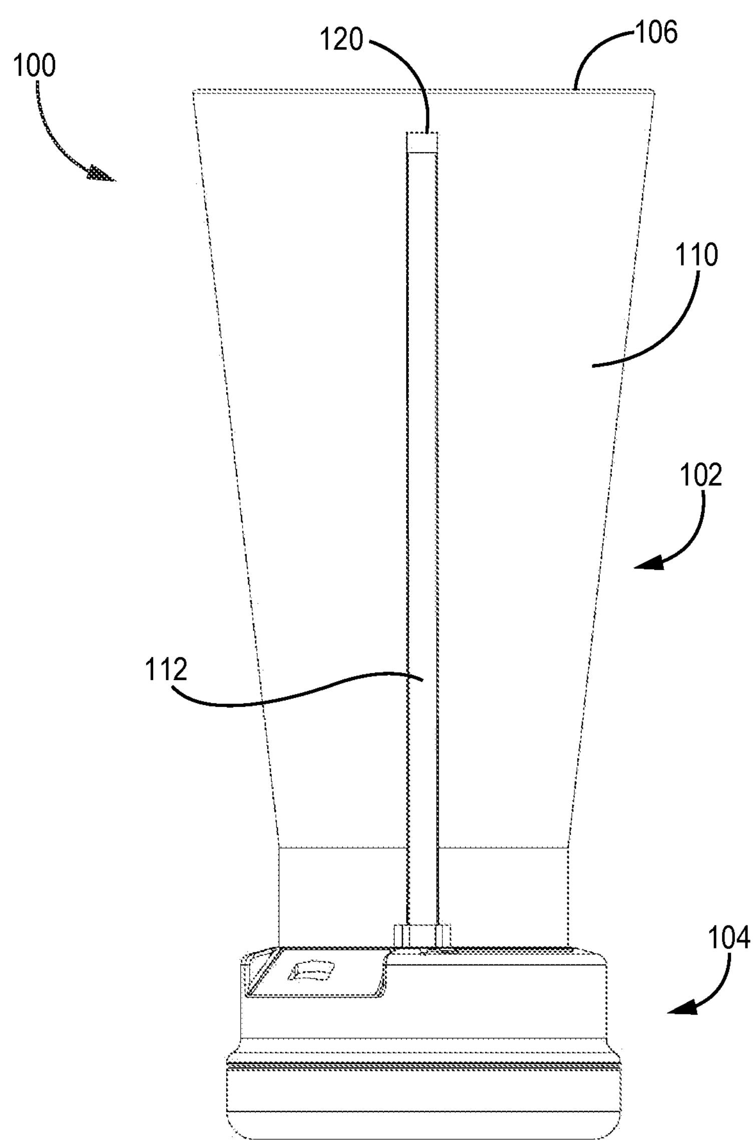
FIG. 1C is a side view of an exemplary embodiment of the urine measurement device of FIG. 1A without the exterior shield so that the capacitive sensor can be seen.
Figure 1D:
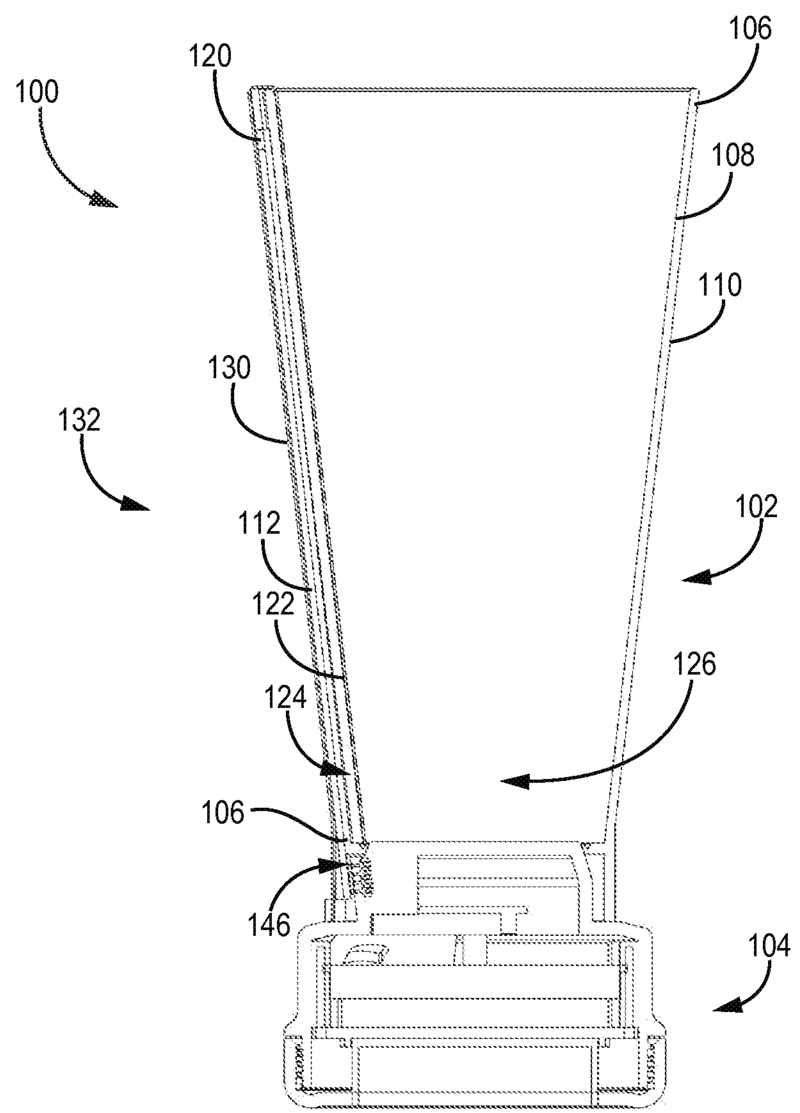
FIG. 1D is a cross-sectional side view of an exemplary embodiment of the urine measurement device of FIG. 1A.
Figure 2A:
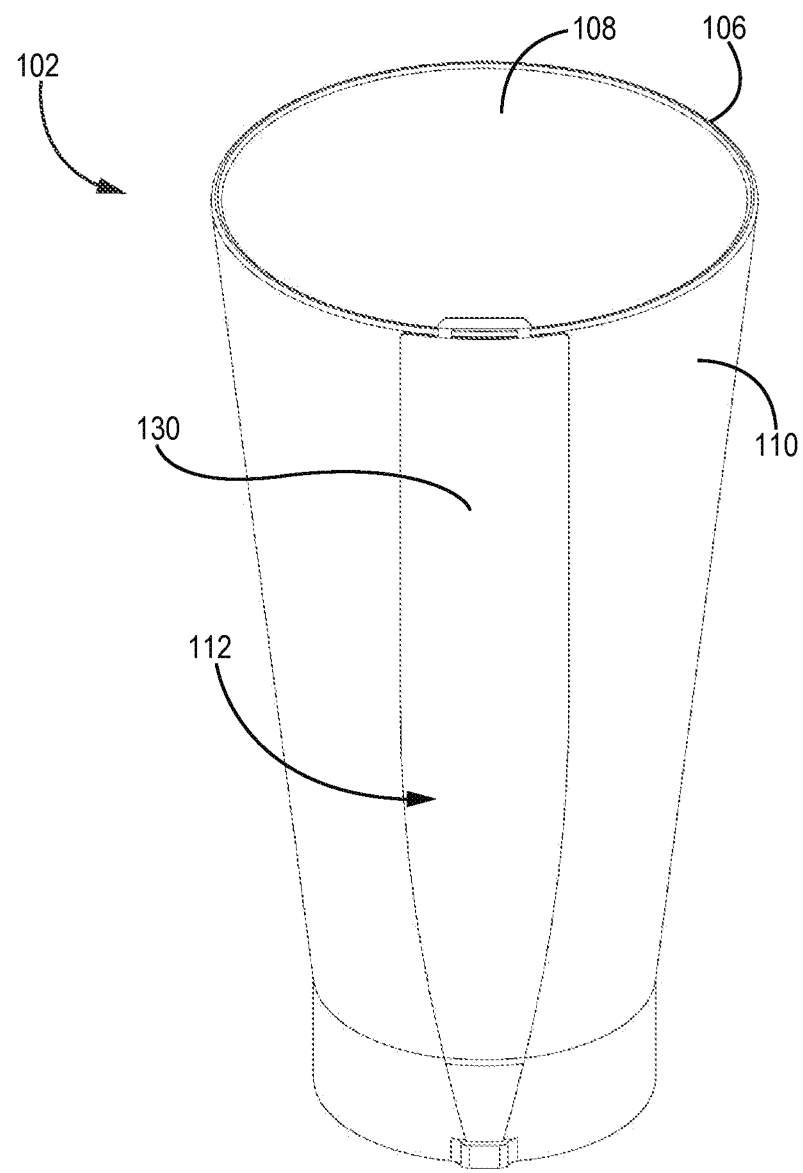
FIG. 2A is a top perspective view of an exemplary embodiment of the container portion of the urine measurement device of FIG. 1A.
Figure 2B:
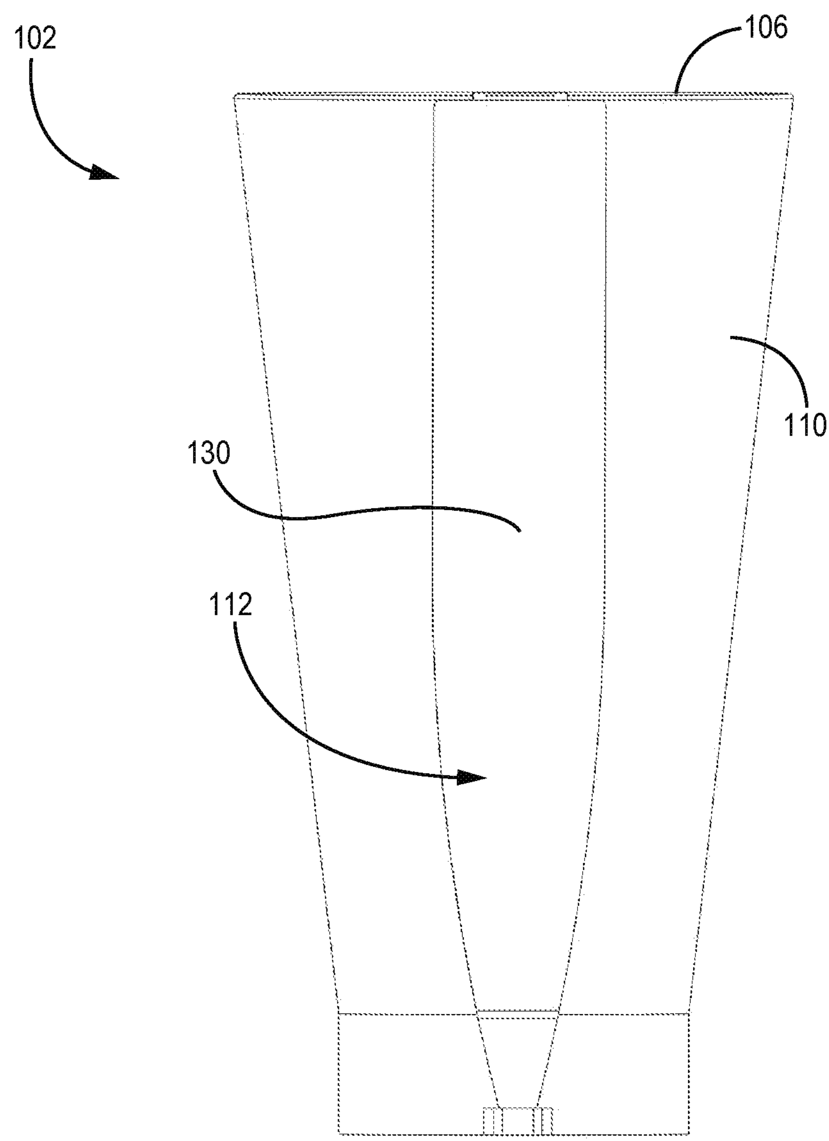
FIG. 2B is a side view of an exemplary embodiment of the container portion of FIG. 2A.
Figure 2C:
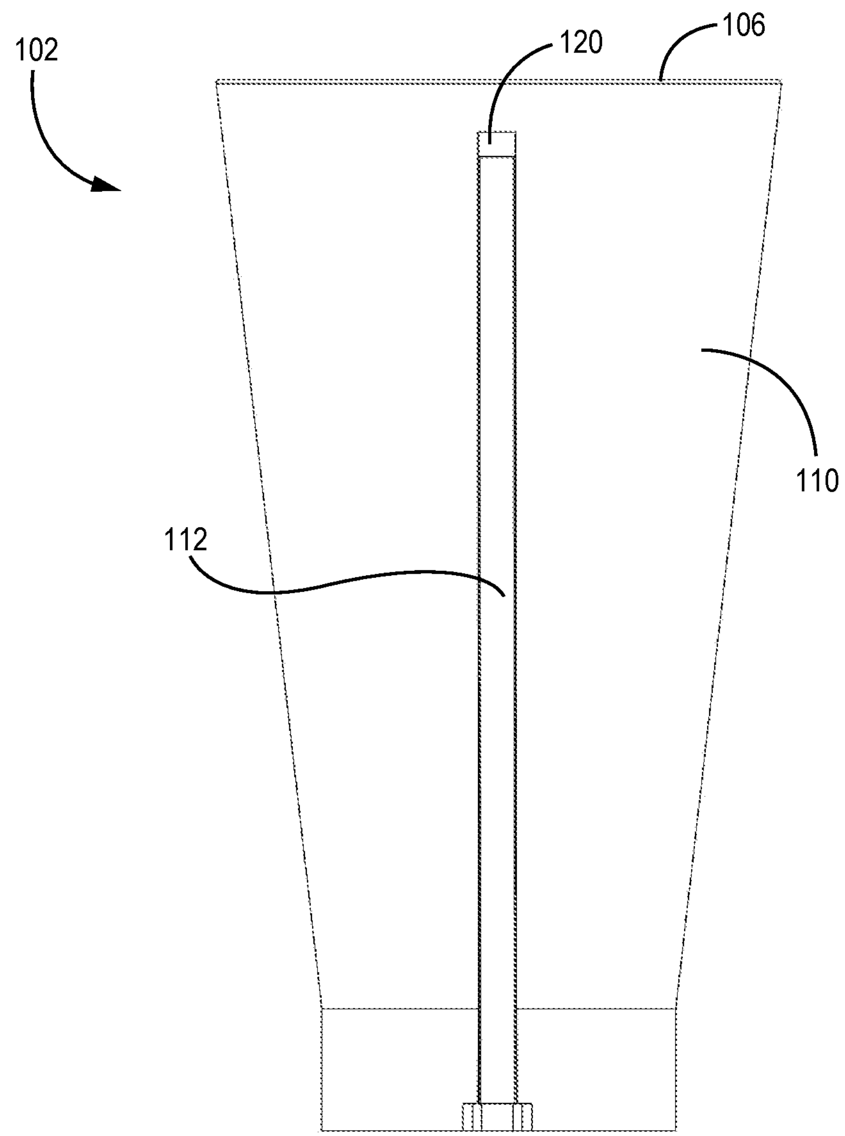
FIG. 2C is a side view of an exemplary embodiment of the container portion of FIG. 2A without the exterior shield so that the capacitive sensor can be seen.
Figure 2D:
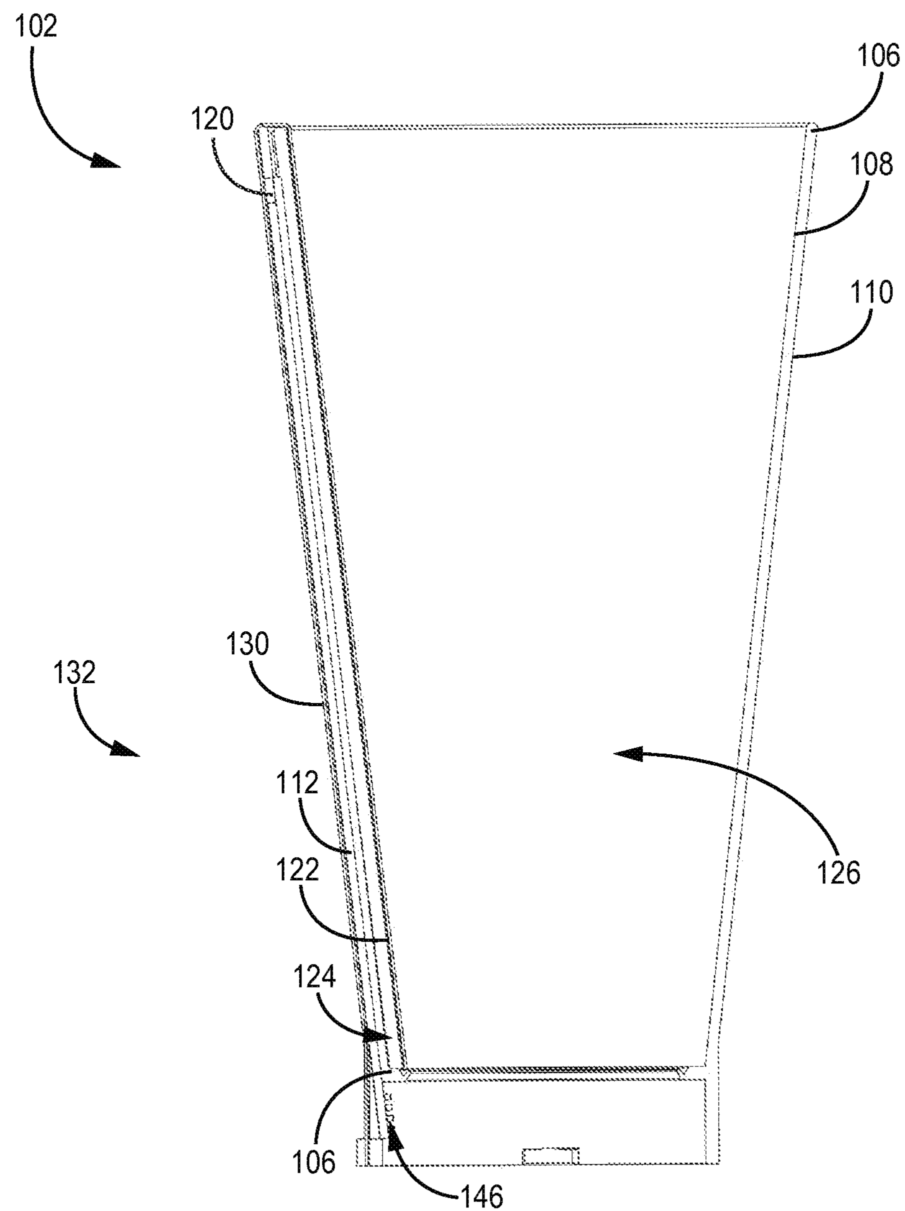
FIG. 2D is a cross-sectional side view of an exemplary embodiment of the container portion of FIG. 2A.
Figure 2E:
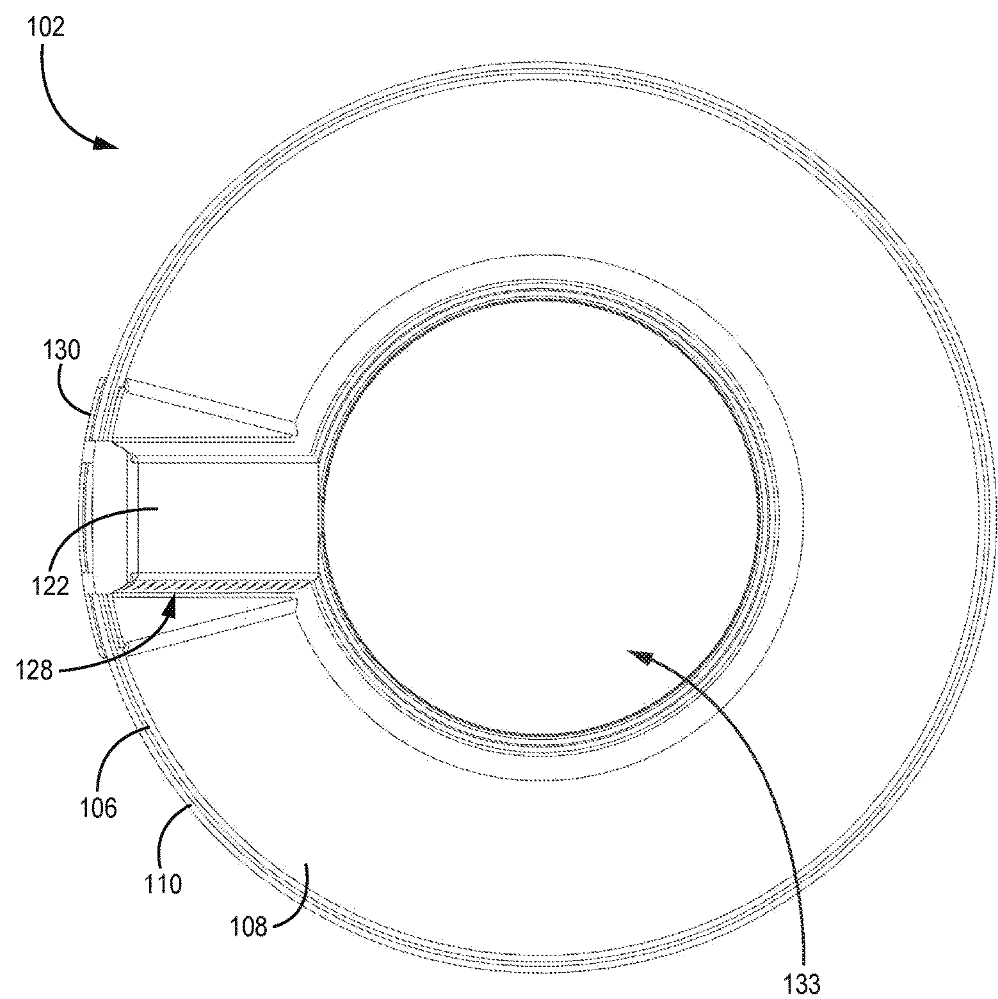
FIG. 2E is a top view of an exemplary embodiment of the container portion of FIG. 2A.
Figure 2F:
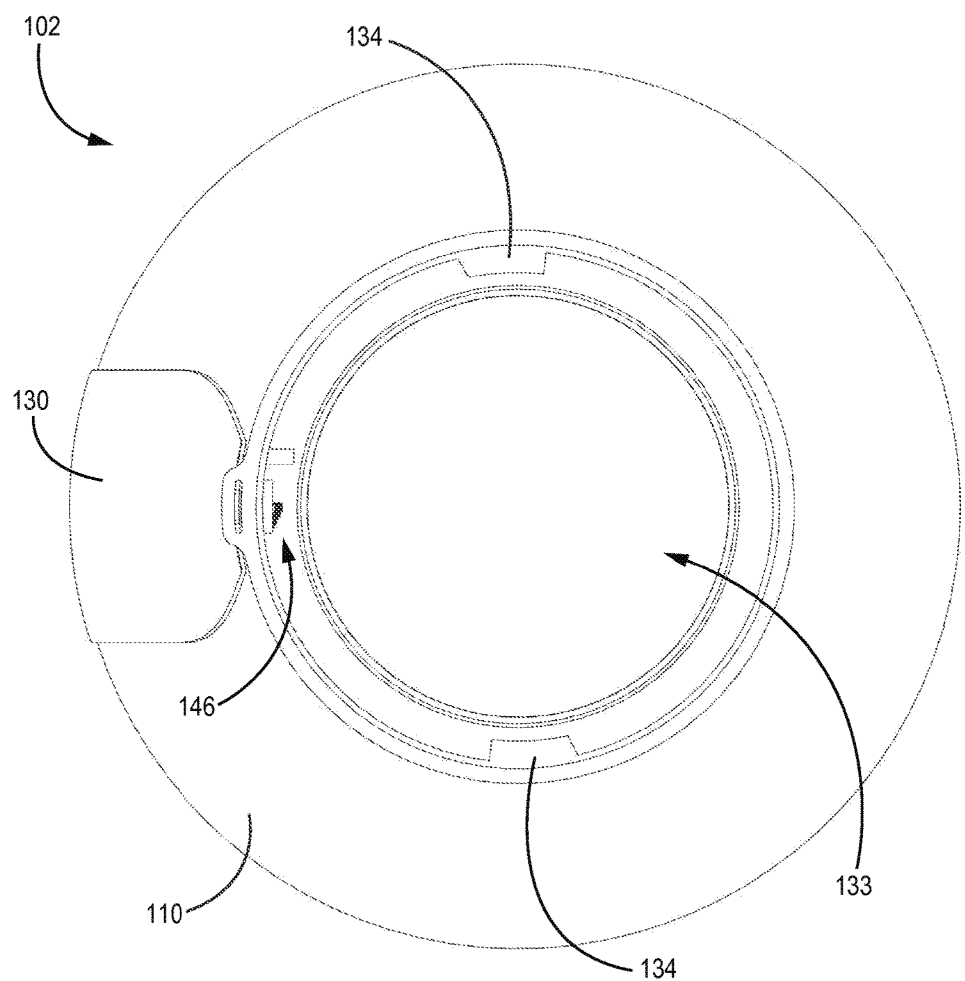
FIG. 2F is a bottom view of an exemplary embodiment of the container portion of FIG. 2A.
Figure 2G:
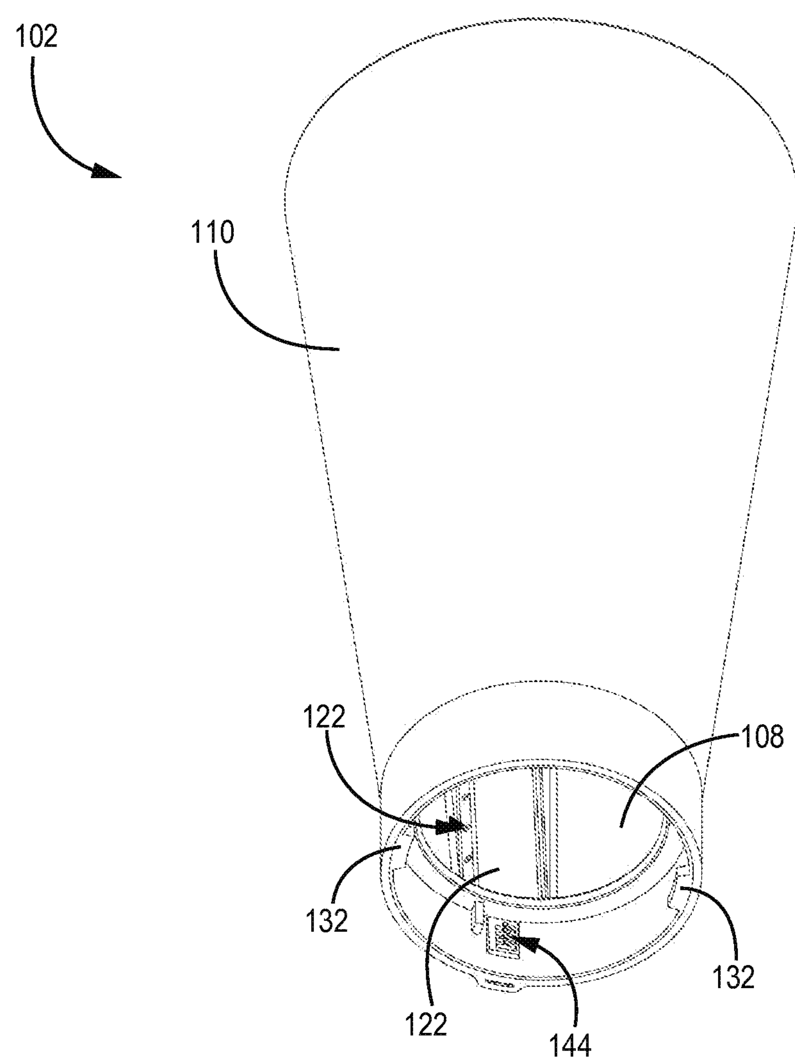
FIG. 2G is a bottom perspective view of an exemplary embodiment of the container portion of FIG. 2A.
Figure 3A:
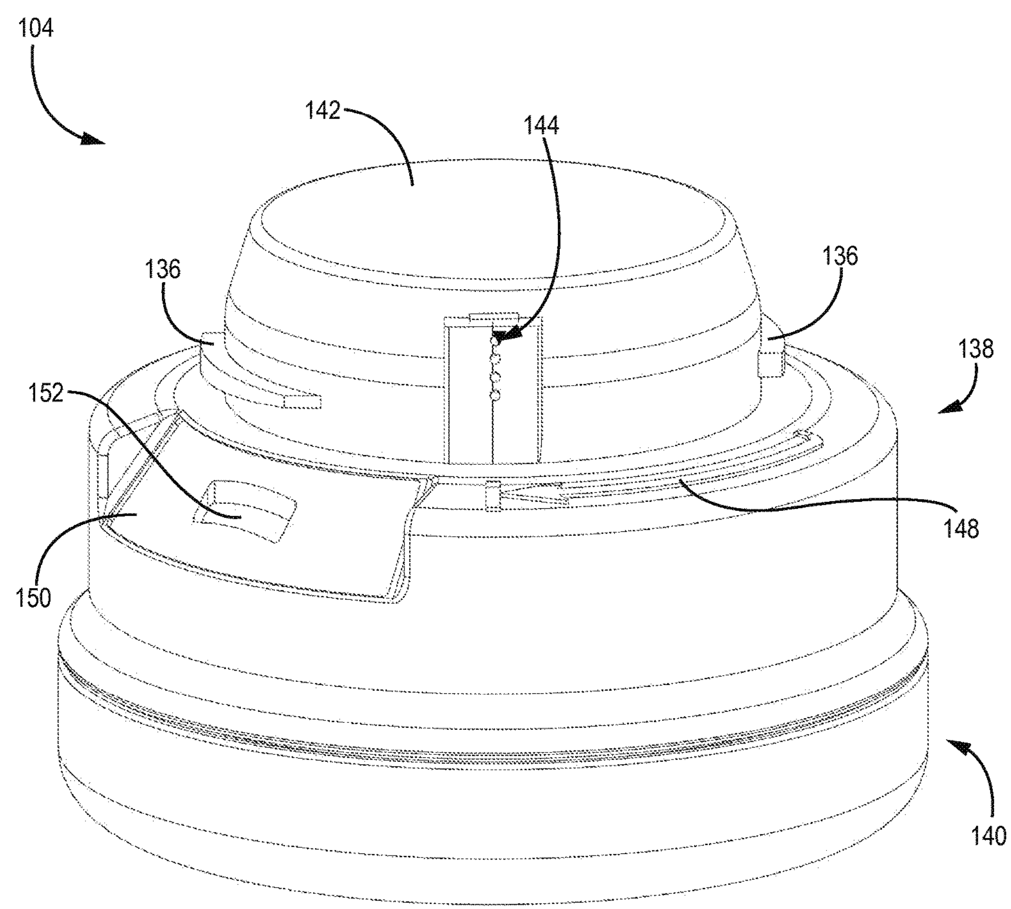
FIG. 3A is a top perspective view of an exemplary embodiment of the electronics portion of the urine measurement device of FIG. 1A.
Figure 3B:
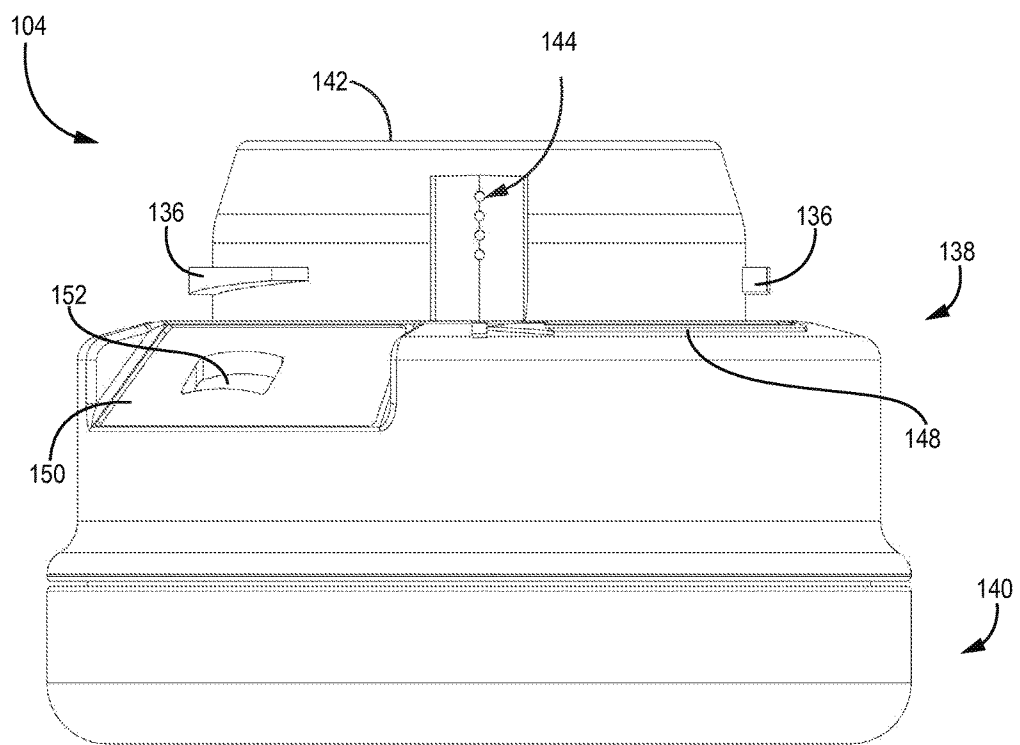
FIG. 3B is a side view of an exemplary embodiment of the electronics portion of FIG. 3A.
Figure 3C:
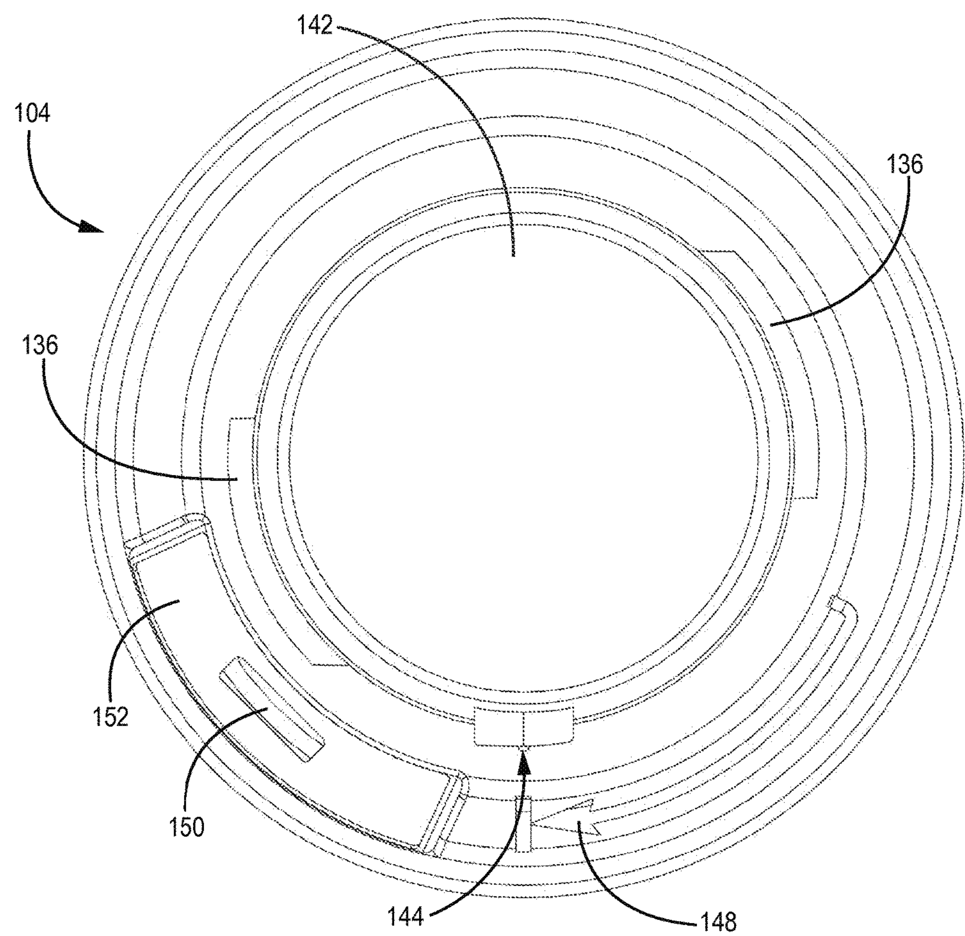
FIG. 3C is a top view of an exemplary embodiment of the electronics portion of FIG. 3A.
Figure 4:
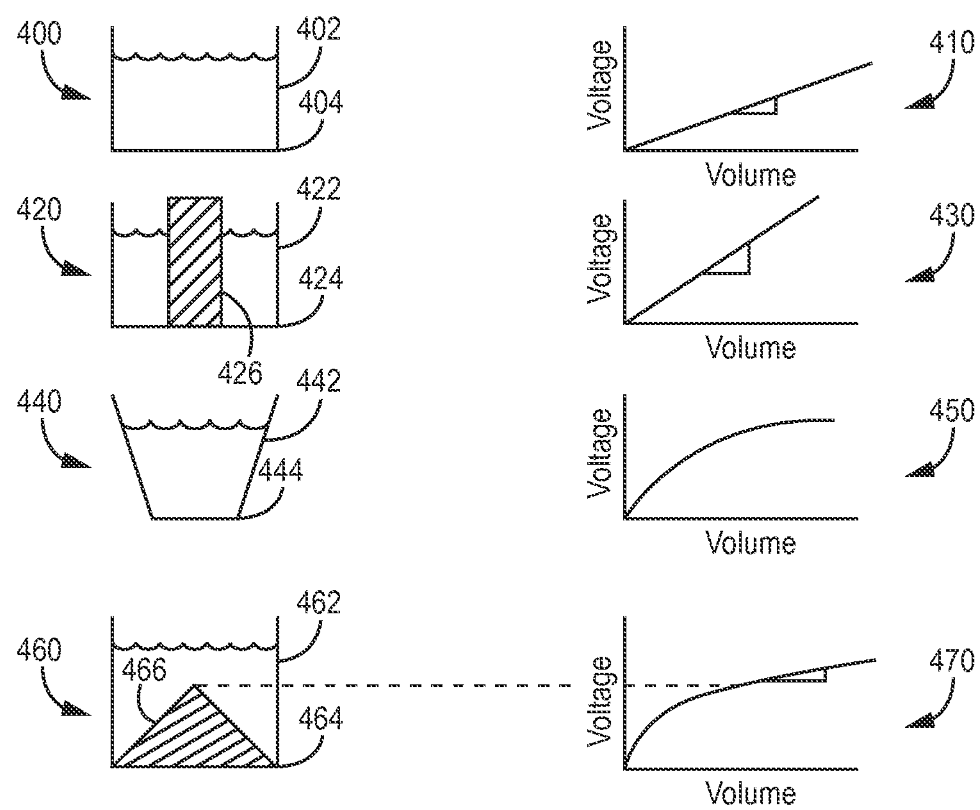
FIG. 4 shows different embodiments of the impact on the relationship between voltage and volume due to different geometries of the container portion and/or electronics portion of the urine measurement device of FIG. 1A.
Figure 5:
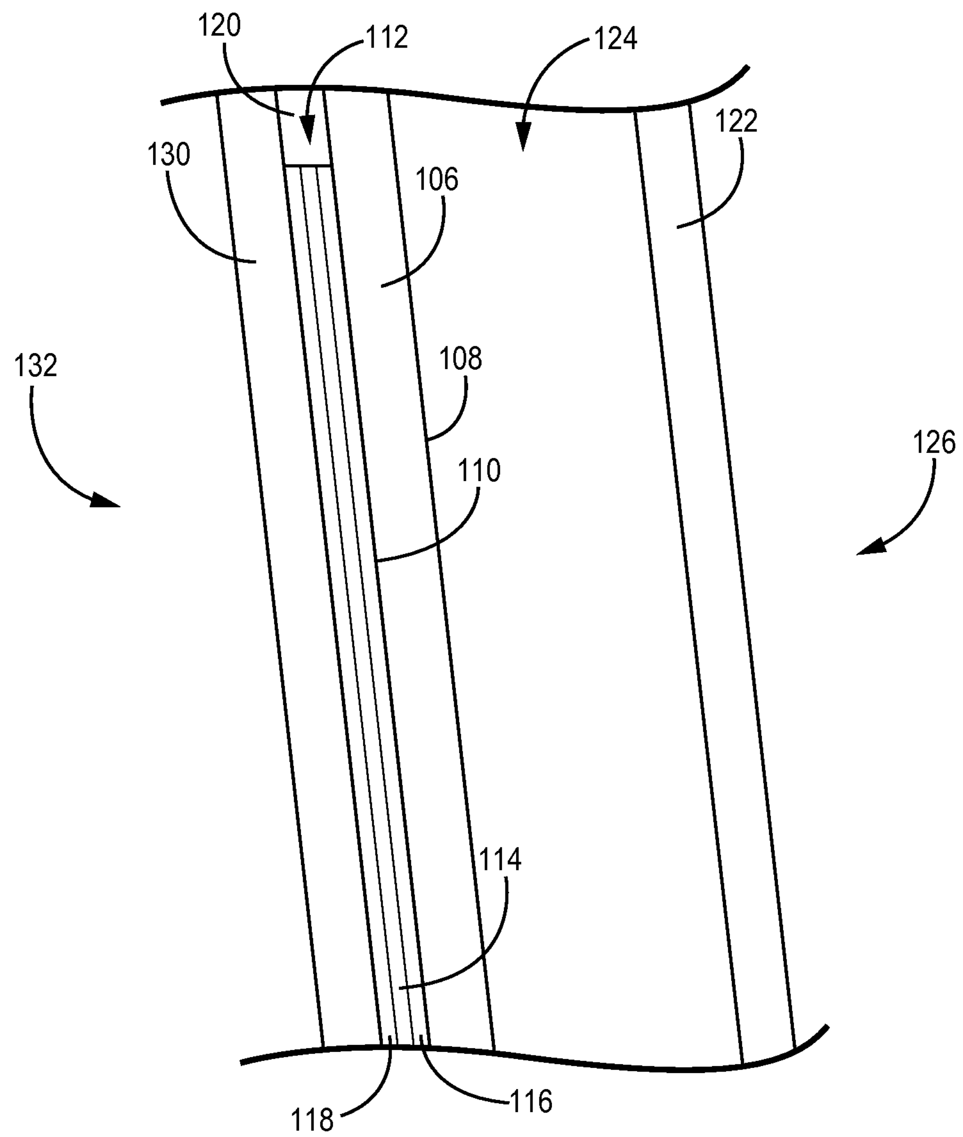
FIG. 5 is an enlarged cross-sectional side view of a portion of an exemplary embodiment of the urine measurement device of FIG. 1A.

FIGS. 1A-1D show different views of an exemplary embodiment of a urine measurement device 100 (or another fluid measurement device or another substance measurement device), including a container portion 102 and an electronics portion 104. FIG. 1A is a perspective view of the urine measurement device 100, FIG. 1B is a side view of the urine measurement device 100, FIG. 1C is a side view of the urine measurement device 100, without at least one exterior shield 130 such that capacitive sensor 112 positioned in the channel 120 can be seen, and FIG. 1D is a cross-sectional side view of the urine measurement device 100 rotated 90 degrees from FIGS. 1B and 1C. FIGS. 2A-2G show different views of an exemplary embodiment of the container portion 102 of the urine measurement device 100. FIG. 2A is a perspective view of the container portion 102, FIG. 2B is a side view of the container portion 102, FIG. 2C is a side view of the container portion 102 without the at least one exterior shield 130 such that capacitive sensor 112 positioned in the channel 120 can be seen, FIG. 2D is a cross-sectional side view of the container portion 102 rotated 90 degrees from FIGS. 2B and 2C, FIG. 2E is a top view of the container portion 102, FIG. 2F is a bottom view of the container portion 102, FIG. 2G is a bottom perspective view of the container portion 102. FIGS. 3A-3C show different views of an exemplary embodiment of the electronics portion 104 of the urine measurement device 100. FIG. 3A is a perspective view of the electronics portion 104, FIG. 3B is a side view of the electronics portion 104, and FIG. 3C is a top view of the electronics portion 104. FIG. 4 shows different embodiments of the impact on the relationship between voltage and volume due to different geometries of the container portion 102 and/or electronics portion 104. FIG. 5 is an enlarged cross-sectional side view of the curved side-wall 106, capacitive sensor 112, interior shield 122, and exterior shield 130 of the container portion 102 of the urine measurement device 100. The description below describes features shown in FIGS. 1A-1C, FIGS. 2A-2F, FIGS. 3A-3C, FIG. 4, and FIG. 5.

In exemplary embodiments, the urine measurement device 100 is a hand-held device for use by men and/or women while voiding/urinating. In exemplary embodiments, funnels and/or other attachments are placed on top of the container portion 102 and may have different shapes for male and female users. In exemplary embodiments, the funnel and/or geometry of the container portion 102 aid in minimizing splash back from urine or other substance that enters into the container portion 102. In exemplary embodiments, the device can be attached in or on the toilet so that the user can be seated on the toilet during the measurement. In exemplary embodiments, the hand-held nature of the urine measurement device 100 introduces potential issues such as tilting and/or shaking of the urine measurement device 100 that may cause measurement errors of flow rate, fluid height, volume, etc. Features of the urine measurement device 100 described herein mitigate the effects of and/or reduce the likelihood of occurrence of the tilting and/or shaking of the urine measurement device.

The container portion 102 can be various shapes and sizes and can include or not include bottom walls and/or top walls. In exemplary embodiments, the container portion 102 includes a curved side-wall 106 having an interior surface 108 and an exterior surface 110, but does not include any top or bottom walls. Accordingly, in some embodiments, the container portion 102 is referred to as a sleeve, without a top or bottom. In these embodiments, the container portion 102 is only able to contain urine, another fluid, and/or substance once it is physically attached to the electronics portion 104, where the top surface of the electronics portion 104 serves as a bottom wall for the container portion 102. In other exemplary embodiments, the container portion 102 includes a bottom wall 133 having an interior surface and an exterior surface, such that the container portion can contain urine, another fluid, and/or other substance even when it is not physically attached to the electronics portion 104. In exemplary embodiments, the container portion 102 includes at least one coupling element 134 (such as threads, bayonet mounts, friction fit, tabs, clips, and/or fasteners) complimentary to at least one coupling element 136 on the electronics portion 104. While the container portion 102 is generally referred to as having a curved side-wall 106, it is understood that embodiments of the container portion 102 can have straight side-walls and have different geometries.

The volume to height ratio of the container portion 102 is related to the geometry of the container portion 102. Accordingly, the resolution of the urine measurement device 100 is a function of the geometry of the container portion 102 which holds the urine, other fluid, and/or other substance. In exemplary embodiments, the side-wall 106 of the container portion 102 includes a conical taper outward from a narrow bottom section to a wider top section (similar in shape to an ice cream cone). In exemplary embodiments, the conical taper provides higher resolution at lower volumes and lower resolution at higher volumes, such that the relationship between height and volume is non-linear throughout the container portion 102. For example, one millimeter of increased fluid height near the bottom of the container portion 102 may equal one milliliter of volume, while one millimeter of increased fluid height near the top of the container portion 102 may equal 5 milliliters of volume (in other words, 1 millimeter of height change near the bottom of the container portion 102 gives the same voltage change as 1 millimeter of height change near the top of the container portion 102, while the volume change would be smaller near the bottom of the container portion 102 than near the top of the contain portion 102—an increased change in voltage per change in volume results in higher resolution). In exemplary embodiments, the software and electronics in the electronics portion 104 accounts for the taper and relationship between height and volume in the various sections of the tapered container portion 102 into account when calculating volume and/or flow rate of the urine, other fluid, and/or other substance. While a container portion 102 having a conical taper is shown in FIG. 1, other embodiments have different shapes, such as the straight non-tapered side-wall 106 in the embodiment of FIG. 7 described below which has a linear relationship between height and volume throughout the tapered container portion 102.

In exemplary embodiments, additional changes can be made to the container portion 102, the electronics portion 104, and/or inserts designed to be placed within the container portion 102 to enable higher resolution at lower volumes. In exemplary embodiments, inserts can be placed into the container portion 102 to augment the height to volume ratio instead of (or in addition to) making changes to the geometry of the container portion 102 itself. In exemplary embodiments, a conical shape which is larger at the bottom and smaller at the top can be inserted into the container portion 102 to achieve similar increased resolution at the bottom of the container portion 102 when the urine, other fluid, and/or other substance first begins to enter the container portion 102 and lower resolution as the urine, other fluid, and/or other substance rises within the container portion 102. In exemplary embodiments where the container portion 102 includes a bottom wall 133, the bottom wall 133 itself can be shaped to increase the resolution throughout the container portion 102 or at lower portions of the container portion 102. In exemplary embodiments, the top surface of the electronics portion 104 can extend up into the container portion 102 in various shapes, such as a rod, cone, pyramid, etc. By allowing for different shaped container portions 102, electronics portions 104, and or the addition of different shaped inserts, the urine measurement device 100 can be customized based on the user's needs. For example, if the user is a pediatric patient, an older patient, or any other patient producing lower quantities of urine at each voiding event, the urine measurement device 100 can be augmented to have increased resolution at lower volumes.

In exemplary embodiments, changing the geometry changes the data output profile and the relationship between voltage and volume at different geometries. Exemplary embodiments of the impact on the relationship between voltage and volume to different geometries is shown in FIG. 4. Geometry 400, with a straight vertical side-wall 402 and a flat bottom surface 404 results in a linear relationship between voltage and volume as shown in graph 410, having a constant slope throughout the volume of the geometry 400. Geometry 420, with a straight vertical side-wall 422, a flat bottom surface 424, and a cylindrical shaped center insert 426 results in a linear relationship between voltage and volume as shown in graph 430, having a constant slope throughout the volume of the geometry 420 that is steeper that the slope in graph 410. Geometry 440, with a tapered sidewall 442 and a flat bottom surface 444 results in a non-linear relationship between voltage and volume as shown in graph 450, having a changing slope throughout the volume of the geometry 440. Geometry 460, with a straight side-wall 462, a flat bottom surface 464, and a conical shaped center insert 466 results in a partially linear and partially non-linear relationship between voltage and volume as shown in graph 470, having a non-constant slope portion within the height ranges corresponding to a bottom portion of the volume that includes the conical shaped center insert 464 and a constant slope portion in the height ranges corresponding to a top portion of the volume that does not include the conical shaped center insert 464.

In exemplary embodiments, the container portion 102 includes a capacitive sensor 112, though it is understood that other types of sensors, such as resistive, magnetic, optical (visible light based, infrared light based, laser based, machine vision based), mechanical (such as weight based, pressure based, float based), radio-wave (such as radar based), acoustic (such ultrasound or infrasound) and capacitive ladder sensors can also be used. In exemplary embodiments, the capacitive sensor 112 (or other sensor or sensing device) is configured to measure at least one of: (1) a flow rate of the urine, other liquid, or other substance into the container portion 102; (2) a level of the urine, other liquid, or other substance within the container portion 102; and (3) a volume of the urine, other liquid, or other substance within the container portion 102. In exemplary embodiments, the capacitive sensor 112 is located on the exterior surface 110 of the side-wall 106. In exemplary embodiments, the capacitive sensor 112 includes a substrate 114 having a first capacitive plate 116 (acting as a sensor electrode facing the measurement volume inside of the container portion 102) on a first side of the substrate 114 and a second capacitive plate 118 (acting as a reference electrode to get a reference measurement outside the container portion 102) on a second side of the substrate 114 opposite the first side of the substrate 114, such that the substrate 114 is sandwiched between the first capacitive plate 116 and the second capacitive plate 118. In exemplary embodiments, the substrate 114 is made of a non-conductive material while each of first capacitive plate 116 and second capacitive plate 118 are made of conductive material such as aluminum, gold, copper, or an alloy of conductive materials. In exemplary embodiments, the conductive material is selected based on substance that will be detected. In embodiments where the conductor comes into contact with the substance, the conductor may be selected to be less reactive with the substance to be detected. In exemplary embodiments, the width of and/or distance between (and/or other dimensions/geometries) the substrate 114, first capacitive plate 116, and second capacitive plate 118 is selected to achieve various resolutions and gains from the capacitive sensor 112.

Looking to FIG. 5, we can see an enlarged cross-sectional diagram of how the sidewall area of the container portion 102. In exemplary embodiments, the capacitive sensor 112 having the first capacitive plate 116 and the second capacitive plate 118 is mounted such that the first capacitive plate 116 faces the exterior surface 110 of the side-wall 106 and the second capacitive plate 118 faces away from the side-wall 106 toward the surrounding environment. This enables measurement of two capacitance measurements: (1) a first capacitance of a rising liquid level within the side-wall 106 of the container portion 102 as measured by the first capacitive plate 116 through the side-wall 106; and (2) a second capacitance of the environment (such as air) outside of the exterior surface 110 of the side-wall 106 as a reference measurement for comparative purposes with the first capacitance. In exemplary embodiments, electronics within the electronics portion 104 determine at least one of: (1) flow rate of the urine, other liquid, or other substance into the container portion 102; (2) a level of the urine, other liquid, or other substance within the container portion 102; and (3) a volume of the urine, other liquid, or other substance within the container portion 102.

In exemplary embodiments, the first capacitive plate 116 of the capacitive sensor 112 is affixed to the exterior surface 110 of the side-wall 106 by an adhesive, epoxy, or mechanical fastening mechanism. In other exemplary embodiments, the first capacitive plate 116 of the capacitive sensor 112 is affixed to an insulating layer by an adhesive, epoxy, or mechanical fastening mechanism, the insulating layer affixed to the exterior surface 110 of the side-wall 106 by an adhesive, epoxy, or mechanical fastening mechanism. In exemplary embodiments, the capacitive sensor 112 performs best and provides better resolution when placed against a relatively flat surface. In exemplary embodiments, the exterior of the container portion 102 where the capacitive sensor 112 is placed is flat on the exterior. By positioning the capacitive sensor 112 on a flat portion on the exterior surface 110 of the side-wall 106, potential air pockets/gaps between the capacitive sensor 112 and the exterior surface 110 of the side-wall 106 are reduced/minimized, thereby enhancing the resolution of the measurements over placement on a rounded/curved exterior surface 110 of a side-wall 106.

In exemplary embodiments, the quality of the readings from the capacitive sensor 112 depends on the thickness of the side-wall 106 upon which the capacitive sensor 112 is placed. Thicker walls produces lower resolution to reading the fluid level. Thinner walls increase the reading resolution and accuracy. In exemplary embodiments, the wall thickness ($W_T$) of the flat surface of the side-wall 106 of the container portion 102 where the capacitive sensor 112 is placed is between approximately zero centimeters (approximately zero inches) and approximately 1.27 centimeters (approximately ½ inch).

In exemplary embodiments, to avoid thickening the side-wall 106 to create the flat surface, exterior surface 110 of the side-wall 106 includes a channel 120 recessed into the exterior surface 110 of the side-wall 106, where the capacitive sensor 112 is positioned within the channel 120. In exemplary embodiments, the channel 120 assists in positioning, mitigates potential gaps between the capacitive sensor and the exterior surface 110 of the side-wall 106, and improves signal strength of the capacitive measurement of the fluid on the other side of the side-wall 106 because the side-wall 106 material is thinner in the channel 120 than in other areas and the first capacitive plate 116 can more easily sense inside the container portion 102. In exemplary embodiments, the channel 120 assists with the repeatable placement of the capacitive sensor 112 on the exterior surface 110 of the side-wall 106 both laterally and vertically on the exterior cup's surface. In exemplary embodiments, the channel on the exterior surface 110 of the side-wall 106 is between approximately 0 millimeters (approximately 0 inches) and approximately 25.4 millimeters (approximately 1 inch) wide.

In exemplary embodiments, shielding is positioned inside and/or outside of the side-wall 106 of the container portion 102 to protect the capacitive sensor 112 (or other sensor or sensing element) against false readings and/or noise in the signals caused by disturbances inside and/or outside of the side-wall 106 of the container portion 102. In exemplary embodiments, the container portion 102 includes at least one interior shield 122 positioned within the container portion 102 that acts as a mechanical buffer between the urine, other fluid, and/or other substance entering the container portion 102 and the capacitive sensor 112 (or other sensor or sensing element). In exemplary embodiments, the at least one interior shield 122 protects the capacitive sensor 112 (or other sensor or sensing element) from erroneously capturing the falling fluid as it flows into the container portion 102 and serves to dampen motion artifacts from producing tilt and/or tremor fluid volume error. In exemplary embodiments, the at least one interior shield 122 partitions a sensing portion 124 of the container portion 102 off from a non-sensing portion 126 of the container portion 102. In exemplary embodiments, the at least one interior shield 122 blocks the capacitive sensor 112 (or other sensor or sensing element) from sensing what is happening in the non-sensing portion 126 directly.

In exemplary embodiments, the sensing portion 124 is coupled to the non-sensing portion through at least one gap/channel/void/aperture 128 below, around the side, and/or through the at least one interior shield 122. The at least one gap/channel/void/aperture 128 allows a controlled flow of the urine, other liquid, or other substance from the non-sensing portion 126 into the sensing portion 124. By only allowing a controlled flow of the urine, other liquid, or other substance into the sensing portion 124, disturbances, turbulence, and/or slosh in the urine, other liquid, or other substance within the non-sensing portion 126 are reduced within the sensing portion 124. These disturbances, turbulence, and/or slosh can be caused as the urine, other liquid, or other substance enters the non-sensing portion 126 caused by shaking or other movement of the container portion 102 (which could be caused by a hand tremor). As the urine, other fluid, and/or other substance enters the container portion 102, it first enters the non-sensing portion 126 and a portion of the urine, other fluid, and/or other substance enters the sensing portion 124 in a controlled manner through the at least one gap/channel/void/aperture 128. Accordingly, the at least one interior shield 122 acts as a "low-pass" filter for the flow data by protecting the capacitive sensor 112 (or other sensor or sensing element) from the disturbances, turbulence, and slosh of the urine, other fluid, and/or other substance within the non-sensing portion 124.

In exemplary embodiments, the at least one interior shield 122 also is conductive and provides a grounding plane for the capacitance to move to from the first capacitive plate 116 of the first capacitive sensor 112 and through the urine, other fluid, and/or other substance in the sensing portion 124. In exemplary embodiments, the grounding plane provided by the at least one interior shield 122 prevents the electrical field lines originating from the first capacitive plate 116 (the sensor electrode) from passing past the at least one interior shield 122. In exemplary embodiments, the urine, other fluid, and/or other substance within the container portion 102 is electrically connected with the grounding plane provided by the interior shield 122. In exemplary embodiments, the grounding plane created by the at least one interior shield 122 enables flow rate measurements, reduces noise in the signals, and/or enhances the performance and/or quality of the flow and/or volume measurements.

In exemplary embodiments, the capacitive sensor 112 operates on the principle of differential capacitance to measure the height of the urine, other fluid, and/or other substance within the sensing portion 124. In exemplary embodiments, this is done by taking measurements from the first capacitive plate 116 and the second capacitive plate 118 and subtracting them from each other to obtain a differential measurement. In exemplary embodiments, the first capacitive plate 116 is a sensor electrode and is used to measure the height of the urine, other liquid, and/or other substance within the sensing portion 124 of the container portion 102. In contrast, the second capacitive plate 118 is a reference electrode and is used to measure the ambient conditions of a surrounding environment 132. The difference in the measurements take from the first capacitive plate 116 and the second capacitive plate 118 is calculated to generate the differential capacitance measurement. The differential capacitance measurement takes into account environmental factors and reduces the dielectric effects on the desired signal.

In exemplary embodiment, the container portion 102 includes at least one exterior shield 130 positioned outside the container portion 102 and shielding the capacitive sensor 112 from effects in an external environment 132, such as a hand coming near or touching the capacitive sensor 112 and distorting the electrical field (such as by increasing the capacitance) or another type of potential interference from the external environment 132. In exemplary embodiments, at least one exterior shield 130 also is conductive and provides a grounding plane for the electric field lines to move from the second capacitive plate 118 of the first capacitive sensor 112 and through an air gap and to the at least one exterior shield. In exemplary embodiments, the grounding plane provided by the at least one exterior shield 130 prevents the electrical field lines originating from the second capacitive plate 118 (the reference electrode) from passing past the at least one exterior shield 130. In exemplary embodiments, the at least one exterior shield 130 completely covers the capacitive sensor 112 from the environment outside of the container portion 102. In exemplary embodiments the at least one interior shield 122 and the at least one exterior shield 130 are a single piece of material that covers over the top of the edge of the side-wall 106 and the sensing portion 124 of the container portion 102.

While only a single capacitive sensor 112 (or other sensor or sensing element) is described above, in other exemplary embodiments, such as the embodiment described below with reference to FIG. 6, more than one capacitive sensor 112 (or other sensor or sensing element) is included. In exemplary embodiments, the additional capacitive sensors 112 can also be shielded internally by interior shields and externally by exterior shields. In exemplary embodiments, having additional sensors helps with tilt independence to mitigate measurement errors causes by tilting of the container portion 102. Tilt independence can also be achieved through use of a gimbaled handle (see FIG. 9 below) and/or by including inertial sensors (such as accelerometers, gyroscopes, etc.) in the electronics portion 104 and using data from the inertial sensors to compensate for tilt.

In exemplary embodiments, the container portion 102 is disposable and can be used only once or a few times before being disposed of. In other embodiments, the container portion is reusable many times. In exemplary embodiments, the electronics portion 104 is not disposable and is intended to be reused multiple times. In exemplary embodiments, the electronics portion 104 connects to the container portion 102 in different ways, such as at the top of the container portion 102 and/or on the side of the container portion 102. In exemplary embodiments, the electronics portion 104 is built into a handle on the container portion 102.

In exemplary embodiments, the electronics portion 104 is divided into a top portion 138 and a bottom portion 140 that can be separated to access the electronics inside of the electronics portion 104. In exemplary embodiment, the top portion 138 is screwed onto the bottom portion 140 using complimentary threading present on the top portion 138 and the bottom portion 140. In exemplary embodiments, the electronics portion 104 includes a top surface 142 that serves as the bottom surface of the container portion 102 when the container portion does not include a bottom wall. In exemplary embodiments, the at least one coupling element 136 (such as threads, bayonet mounts, friction fit, tabs, clips, and/or fasteners) is complimentary to the at least one coupling element 134. In exemplary embodiments, the at least one coupling element 136 and the at least one coupling element 134 engage after rotating the container portion 102 onto the electronics portion 104. In exemplary embodiments, when the at least one coupling element 136 engages with the at least one coupling element 134, a liquid tight seal is created between the top surface 142 and the bottom of the container portion 102.

In exemplary embodiments, the electronics portion 104 includes electrical contacts 144 that connect with corresponding electrical contacts 146 electrically connected to the capacitive sensor 112 of the container portion 102 when the at least one coupling element 136 engages with the at least one coupling element 134. In exemplary embodiments, the electronics portion 104 includes at least one alignment indicator 148 configured to aid in alignment of the at least one coupling element 136 with the at least one coupling element 134 when connecting the electronics portion 104 to the container portion 102. In exemplary embodiments, the at least one alignment indicator 148 is a visual and/or tactile alignment indicator. In exemplary embodiments, a corresponding alignment indicator is also present on the container portion 102. In exemplary embodiments, the at least one alignment indicator 148 includes coloring and the container portion 102 includes corresponding coloring.

In exemplary embodiments, the electronics portion 104 includes at least one button 150 and/or at least one electronic indicator 152. In exemplary embodiments, the button can be pressed by the user to indicate the beginning and/or end of a voiding event during which measurement occurs. For example, the user could press the at least one button 150 before urinating into the container portion 102. The push of the at least one button 150 at this time can trigger a new voiding event file to be created by the electronics components within the electronics portion 104 and/or for a counter/timer marker to be placed into a file by the electronics components within the electronics portion 104. In exemplary embodiments, the user could press the at least one button 150 after completion of the voiding event once urination is completed. The push of the at least one button 150 at this time can trigger a counter/timer market to be placed into the file by the electronics components within the electronics portion 104, for writing to the file to be terminated, and/or for the file to be closed. In exemplary embodiments, writing to the file can be terminated and/or the file closed by the electronics components within the electronics portion 104 after the flow rate is below a certain threshold for a certain amount of seconds.

In exemplary embodiments, the electronics portion 104 can be activated in other ways rather than pressing a button or switch, such as by: (1) sensing the presence of urine, other fluid, and/or other substance within the container portion 102; (2) motion detection; (3) a sensor configured to detect when someone is holding the device; and/or (4) detection of when the electronics portion 104 is coupled with a container portion 102.

In exemplary embodiments, the at least one electronic indicator 152 includes at least one of a visual, audible, and haptic alert. For example, at least one of a visual, audible, and haptic alert can occur when: (1) the container portion 102 is properly connected with the electronics portion 104 once the at least one coupling element 136 and the at least one coupling element 134 are properly engaged; (2) the urine measurement device 100 and/or electronics portion 104 are functioning properly (such as to confirm operation after the urine measurement device 100 and/or electronics portion 104 were dropped); and (3) that the urine measurement device 100 is fully function (batter level is adequate, container portion 102 is operating correctly, electronics portion 104 is operating correctly, electrical contact between the container portion 102 and the electronics portion 104 is acceptable, humidity and/or temperature is within operation range.

In exemplary embodiment, the at least one electronic indicator 152 is used to indicate when the at least one button 150 has been pressed and/or when the measurement is in progress or completed. In exemplary embodiments, the electronics portion 104 provides spoken instructions and/or status updates to the user, such as indications that the "device is fully function" or requests for the user to "insert a sleeve". In exemplary embodiments, audible beeps indicate operation and/or status updates to the user. In exemplary embodiments, the electronics portion 104 includes a more complex human machine interface (HMI) for user interaction with the urine measurement device 100. In exemplary embodiments, the HMI includes any combination of input and/or display devices, including for example light emitting diode (LED) indicators, Liquid Crystal Display (LCD) displays, e-ink displays, and/or touch screens, buttons, switches, dials, cameras, etc. In exemplary embodiments, haptic alerts include vibration.

In exemplary embodiments, the urine measurements are taken by the urine measurement device 100 within a preferred operating environment where the operational relative humidity (RH) range between approximately zero and approximately eighty percent relative humidity and within the operational temperature range between approximately 10 degrees Celsius (approximately 50 degrees Fahrenheit) and approximately 38 degrees Celsius (approximately 100 degrees Fahrenheit). In exemplary embodiments, the urine measurement device 100 further includes temperature and/or humidity compensation circuitry including temperature and/or humidity sensors included within the container portion 102 and/or the electronics portion 104.

In exemplary embodiments, the urine measurement device 100 is calibrated soon before taking measurements to account for current environmental conditions, such as the relative humidity (RH) and/or the temperature. In exemplary embodiments, to establish environmental conditions at the time of measurement, the user "teaches" (calibrates) the capacitive sensor 112 as to what capacitance values are present at 0 percent urine, other fluid, and/or other substance height, equating that capacitance to the lowest possible output voltage of the sensor, and what capacitance values are present at 100 percent urine, other fluid, and/or other substance height, equating that capacitance to the highest possible output voltage of the sensor. This calibration/zeroing/taring step effectively normalizes variances in temperature and humidity just prior to taking actual urine, other fluid, and/or another substance height data.

In exemplary embodiments, manual calibration is performed prior to use according to the following steps: (1) the user turns on the device with no urine, other fluid, and/or another substance in the container portion 102, automatically teaching the sensor at a zero percent urine, other fluid, and/or another substance height; (2) the user then fills the container portion with water, past a specified level indicated on the container portion; (3) the user then pushes a calibration button, teaching the sensor a 100 percent urine, other fluid, and/or another substance height. After the urine measurement device 100 has been calibrated in the current environment, the user can then empty out the container portion 102 and use the urine measurement device 100 to record their voiding event.

In exemplary embodiments, calibration is performed prior to use according to the following: (1) a piece of conductive material is adhered to the inside of the container portion 102, opposite to where the capacitive sensor 112 is adhered to the container portion 102 (this is likely done at manufacture of the container portion 102); (2) the conductive material is then grounded to simulate a high urine, other fluid, and/or other substance height within the container portion (this is likely done at manufacture of the container portion 102); (3) when the container portion 102 is installed onto the electronics portion 104, the sensor is taught a 100 percent urine, other fluid, and/or another substance height because of the grounded piece of conductive material adhered to the inside of the container portion 102; (4) indicator 140 then indicates to the user that the user should remove the conductive material using a pull-tab from the inside of the sleeve (this could occur via an LED flash and/or other indication); (5) after either a certain period of time or a button press from the user confirming that the conductive material has been removed, the capacitive sensor 112 is taught at zero percent urine, other fluid, and/or other substance height. After the urine measurement device 100 has been calibrated in the current environment, the user can then use the urine measurement device 100 to record their voiding event.

Figure 6:
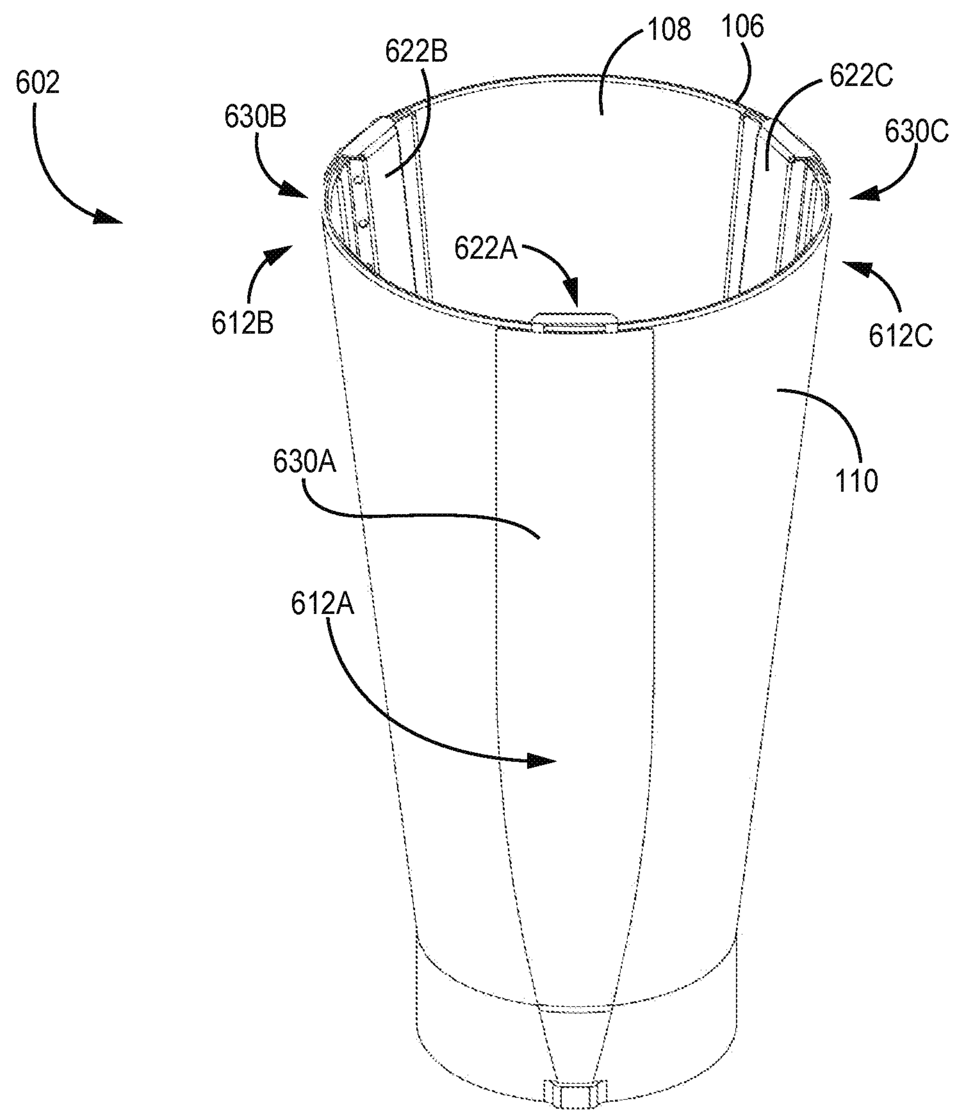
FIG. 6 is a top perspective view of another exemplary embodiment of the container portion of the urine measurement device of FIG. 1A having a plurality of sensors.

FIG. 6 is a perspective view of another exemplary embodiment of the container portion 102 of the urine measurement device 100 that includes a plurality of sensors, hereinafter container portion 602. Container portion 602 includes three separate capacitive sensors 112, hereinafter capacitive sensors 612A, 612B, and 612C. Container portion also includes three separate interior shields 122, hereinafter interior shield 622A, 622B, and 622C. Container portion also includes three separate exterior shields 130, hereinafter exterior shields 630A, 630B, and 630C. Container portion 602 and its component parts operate similarly to the description of container portion 102 above, just that there are signals from each of the capacitive sensors 612A, 612B, and 612C that are sent to the electronics portion 104 for processing and determination of at least one of the flow rate of the substance into the container portion 602, the height of the substance within the container portion 602, and the volume of the substance within the container portion 602. In exemplary embodiments having three capacitive sensors 612A, 612B, and 612C, each of the three capacitive sensors 612A, 612B, and 612C is located approximately 120 degrees from each of the other capacitive sensors 612A, 612B, and 612C. In exemplary embodiments having only two capacitive sensors 612A and 612C, each of the two capacitive sensors 612A and 612B is located approximately 180 degrees from the other capacitive sensor 612A and 612B. By combining the data from the three different capacitive sensors 612A, 612B, and 612C, the urine measurement device 100 using the container portion 602 allows for tilt independence. Specifically, as the container is tilted to one side, while it may not be measured as much by one of the capacitive sensors 612A, 612B, and 612C, it will be measured more by one or more of the other capacitive sensors 612A, 612B, and 612C.

Figure 7:
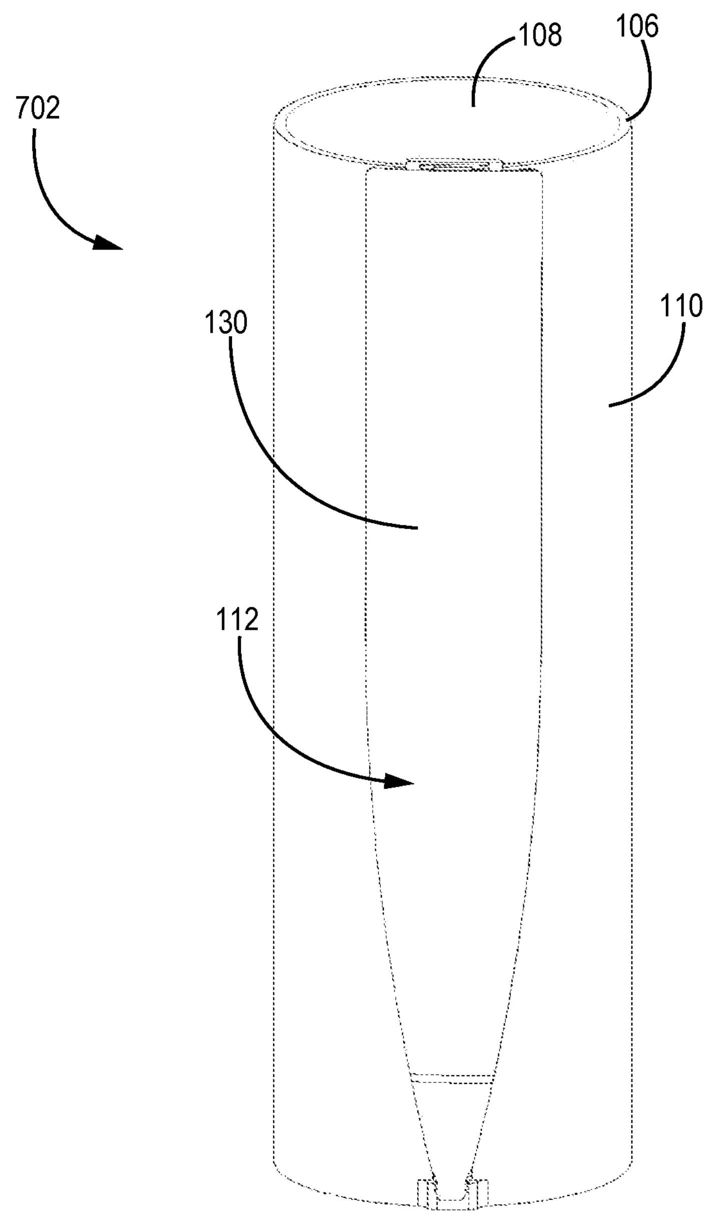
FIG. 7 is a top perspective view of another exemplary embodiment of the container portion of the urine measurement device of FIG. 1A having straight non-tapered sides.

FIG. 7 is a perspective view of another exemplary embodiment of the container portion 102 of the urine measurement device 100 having a straight non-tapered sidewall 106, hereinafter container portion 702.

Figure 8A:
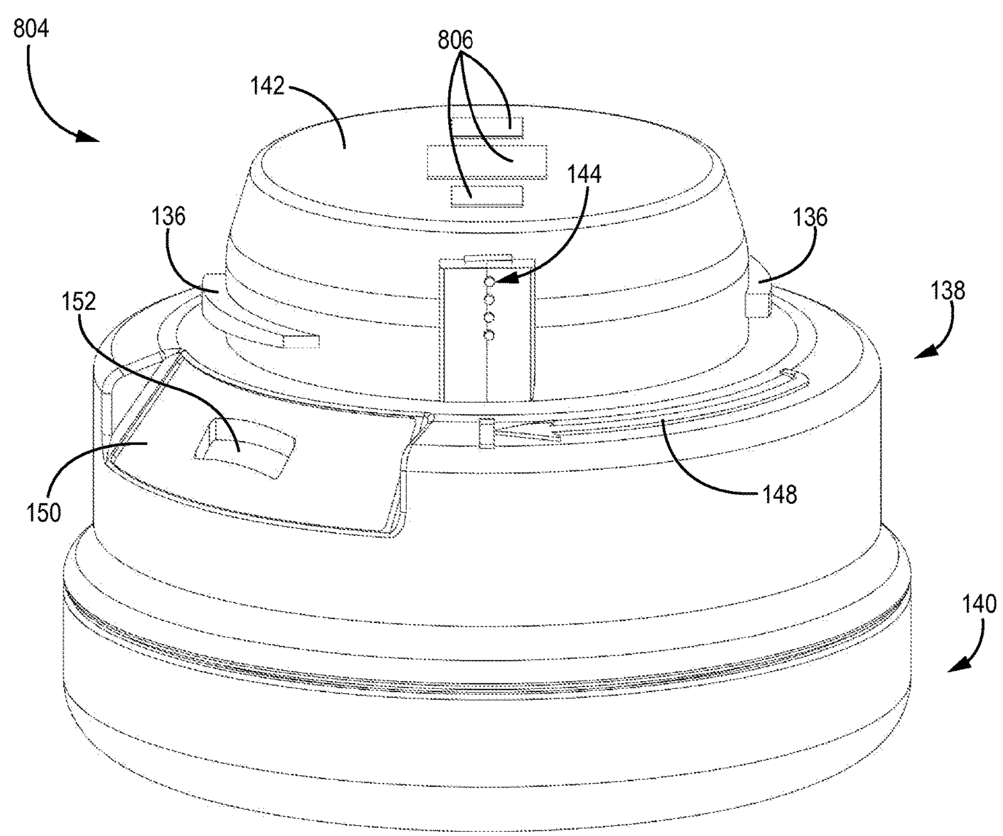
FIG. 8A is a top perspective view of another exemplary embodiment of the electronics portion of the urine measurement device of FIG. 1A having sensors on a top surface of the electronics portion.
Figure 8B:
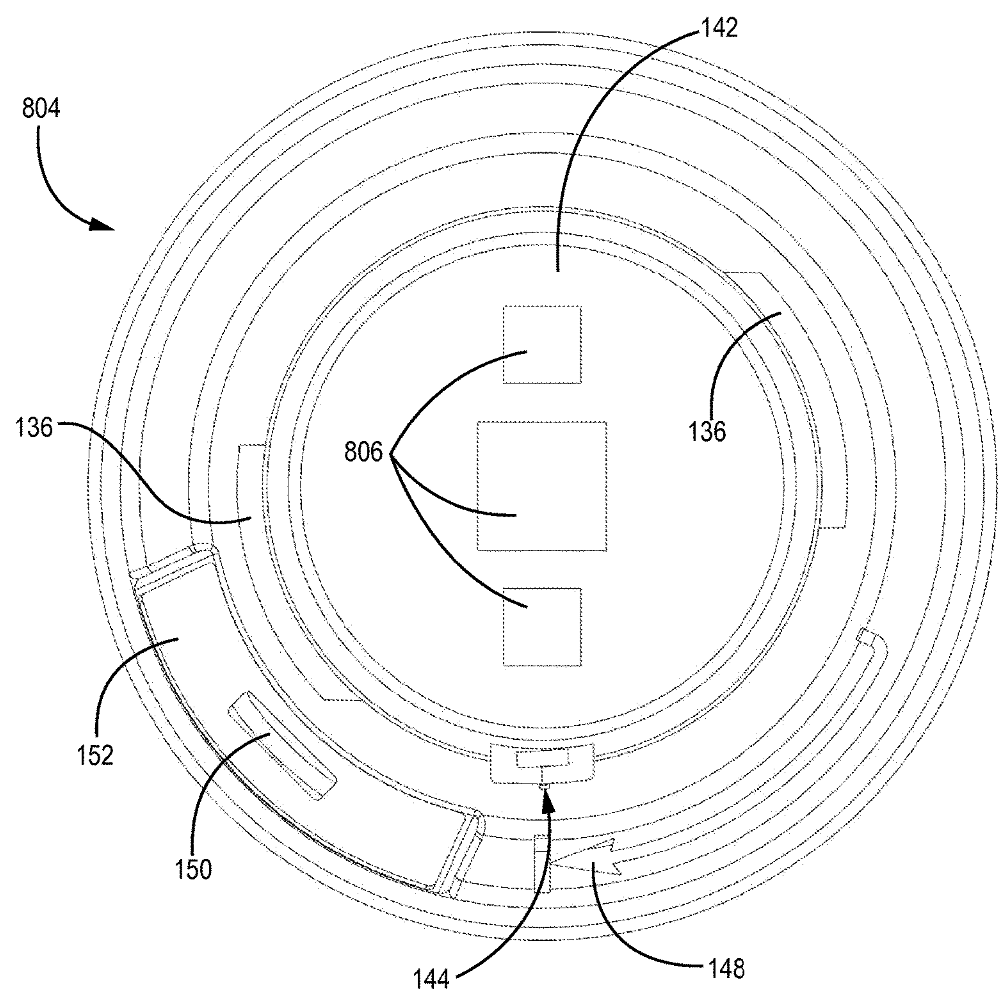
FIG. 8B is a top view of the exemplary embodiment of the electronics portion of FIG. 8A.

FIGS. 8A-8B show different views of another exemplary embodiment of the electronics portion 104 of the urine measurement device 100 having at least one sensor 806 on the top surface 142, referred to herein as electronics portion 804. FIG. 8A is a perspective view of the electronics portion 804 and FIG. 8B is a top view of the electronics portion 804. In exemplary embodiments, each of the at least one sensor 806 are particular sensors designed to sense various properties of the urine, other liquid, or other substance deposited into the container portion 102. In exemplary embodiments, the at least one sensor 806 senses proteins, dissolved solids, sugar levels, gravity, etc. of the urine, other liquid, or other substance deposited into the container portion 102. In exemplary embodiments, one of the at least one sensor 806 determines total dissolved solids (permittivity) in the urine, other liquid, or other substance. In exemplary embodiments, the capacitive sensor 112 and the at least one sensor 806 measuring TDS are not operational at the same time as they may affect each other's readings when they are turned on at the same time. Accordingly, the TDS sensor can be off while the capacitive sensor 112 is on and the capacitive sensor 112 can be off while the TDS sensor is on at synchronized times. In other embodiments, the at least one interior shield 122 isolates the sensors operation enough that the TDS sensor can operate in the non-sensing portion 126 while the capacitive sensor 112 operates in the sensing portion 126 without substantial interference between the two.

Figure 9:
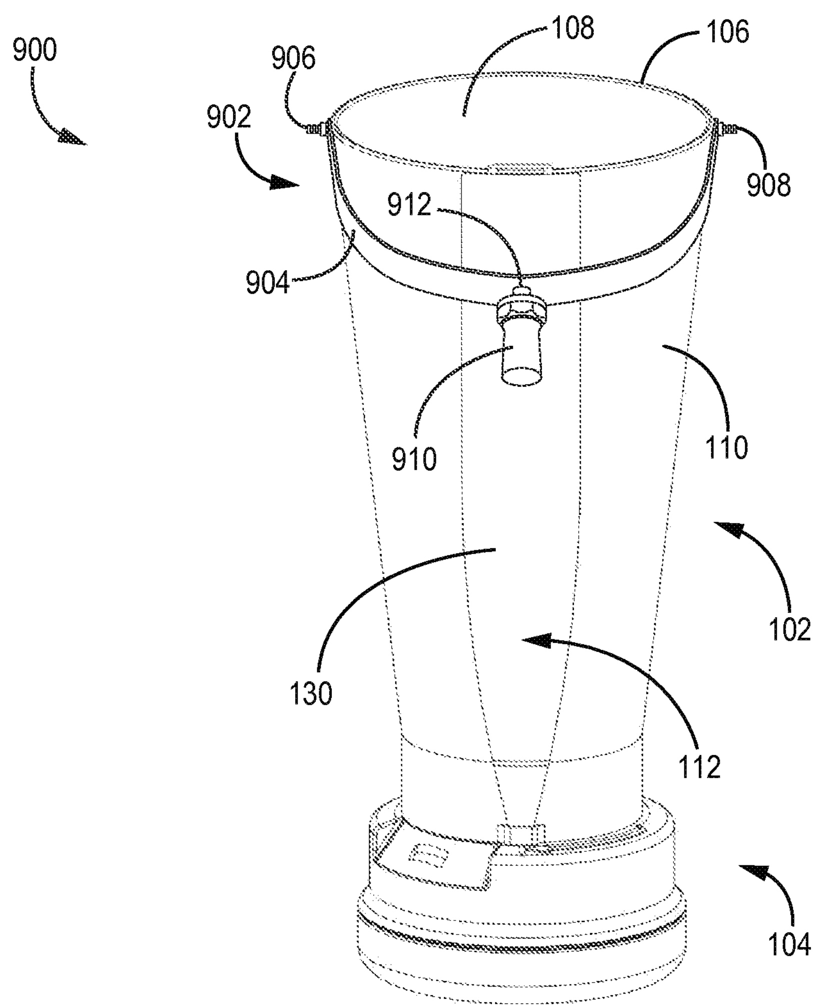
FIG. 9 is a top perspective view of another exemplary embodiment of a urine measurement device, including a container portion, an electronics portion, and a stabilizing handle portion.

FIG. 9 is a perspective view of another exemplary embodiment of a urine measurement device 900, including a container portion 102, an electronics portion 104, and a stabilizing handle portion 902. Urine measurement device 900 includes similar components to urine measurement device 100 described above, which operate as described above. In addition, urine measurement device 900 includes the stabilizing handle portion 902 that aids in leveling the container portion 102 during uroflowmetry even if the user is holding it at an angle or shaking during the measurement. In exemplary embodiments, the stabilizing handle portion 902 includes a connecting bracket 904 connected to the container portion 102 using a first rotating connector 906 and a second rotating connector 908. In exemplary embodiments, the first rotating connector 906 and the second rotating connector 908 enable the connecting bracket 904 to pivot along an axis between the first rotating connector 906 and the second rotating connector 908. In exemplar embodiments, the stabilizing handle portion 902 further includes a handle 910 connected to the connecting bracket 904 using a third rotating connector 912. In exemplary embodiments, the third rotating connector 912 enables the handle 910 to pivot along another axis.

In exemplary embodiments, gravity aids in leveling the container portion 102, based on the weight of the electronics portion 104 and the urine, other liquid, or other substance as it enters the container portion 102. In exemplary embodiments, the stabilizing handle portion 902 enables the container portion 102 to be horizontal to the ground independent of how the handle 910 is positioned by the user. In exemplary embodiments, the ability to pivot around the two axes enables the stabilizing handle portion 902, when held by a user at the handle 910 to suppress undesired tilting of the container portion 102 facilitating more accurate measurement of the flow rate; urine, other fluid, and/or other substance level; and/or urine, other fluid, and/or other substance volume in the container portion 102. While container portion 102 is described with reference to FIG. 9 above, it is understood that any suitable container portion can be used with the stabilizing handle portion 902, such as the other container portions described herein. While the stabilizing handle portion 902 was described with a specific structure herein, it is understood that other types of gimballed stabilizing means and/or swivel balls and/or other mechanical stabilization generally can be used to achieve the desired mechanical tilt independence. Further, while the stabilizing handle portion 902 (and mechanical stabilization for tilt independence generally) is described above as compensating a single capacitive sensor 112 based system, it is understood that the mechanical stabilization described herein can be used to compensate for tilt and/or user shake in systems having more sensors (such as additional capacitive sensors 112) and/or other types of sensors, such as optical (visible light based, infrared light based, laser based, machine vision based), mechanical (such as weight based and pressure based), acoustic (such as ultrasound and/or infrasound), and radio-wave (such as radar based) sensors can also be used to determine at least one of flow rate; urine, other fluid, and/or other substance height; and/or urine, other fluid, and/or other substance volume. In exemplary embodiments, just one of flow rate; urine, other fluid, and/or other substance height; and/or urine, other fluid, and/or another substance volume are determined and the others are determined based on knowledge of additional parameters, such as the geometry of the container portion 102 and the elapsed time.

Figure 10A:
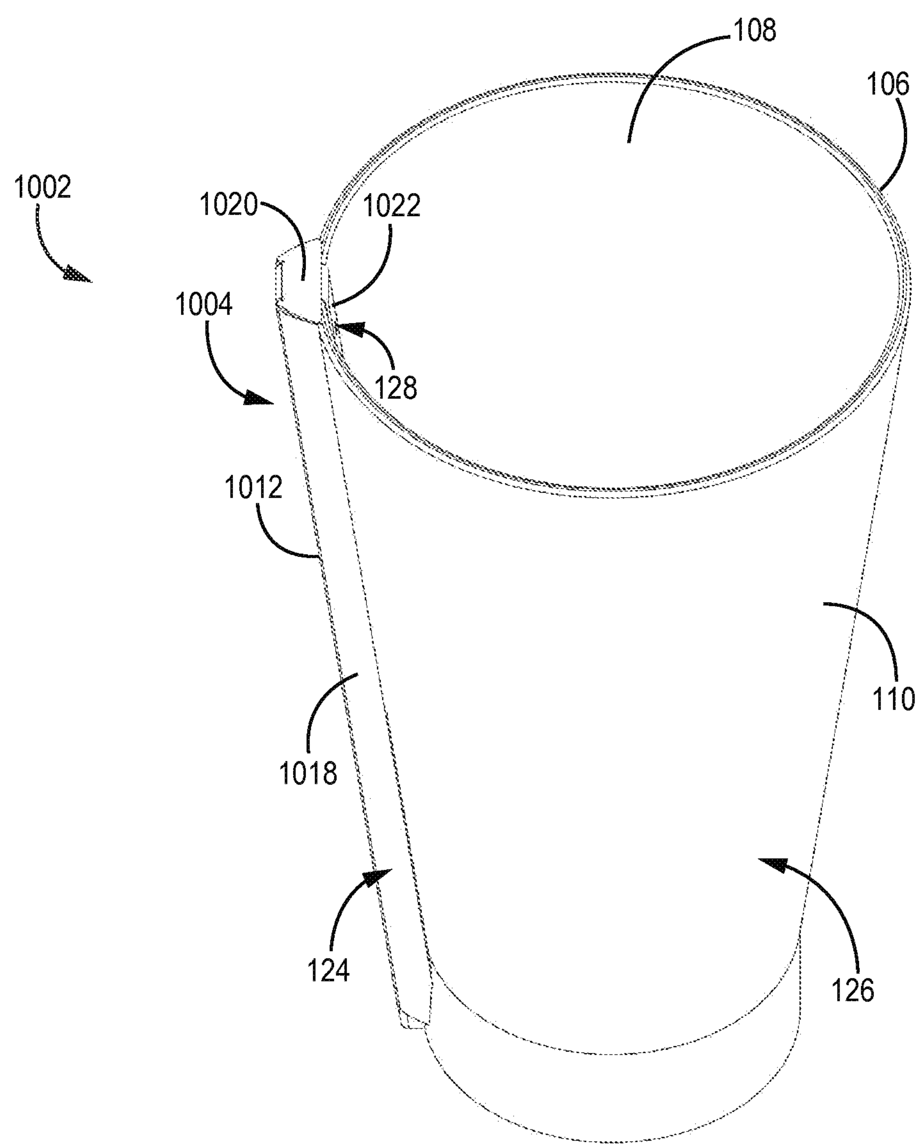
FIG. 10A is a top perspective view of another exemplary embodiment of the container portion of the urine measurement device of FIG. 1A having an outer notched portion.
Figure 10B:
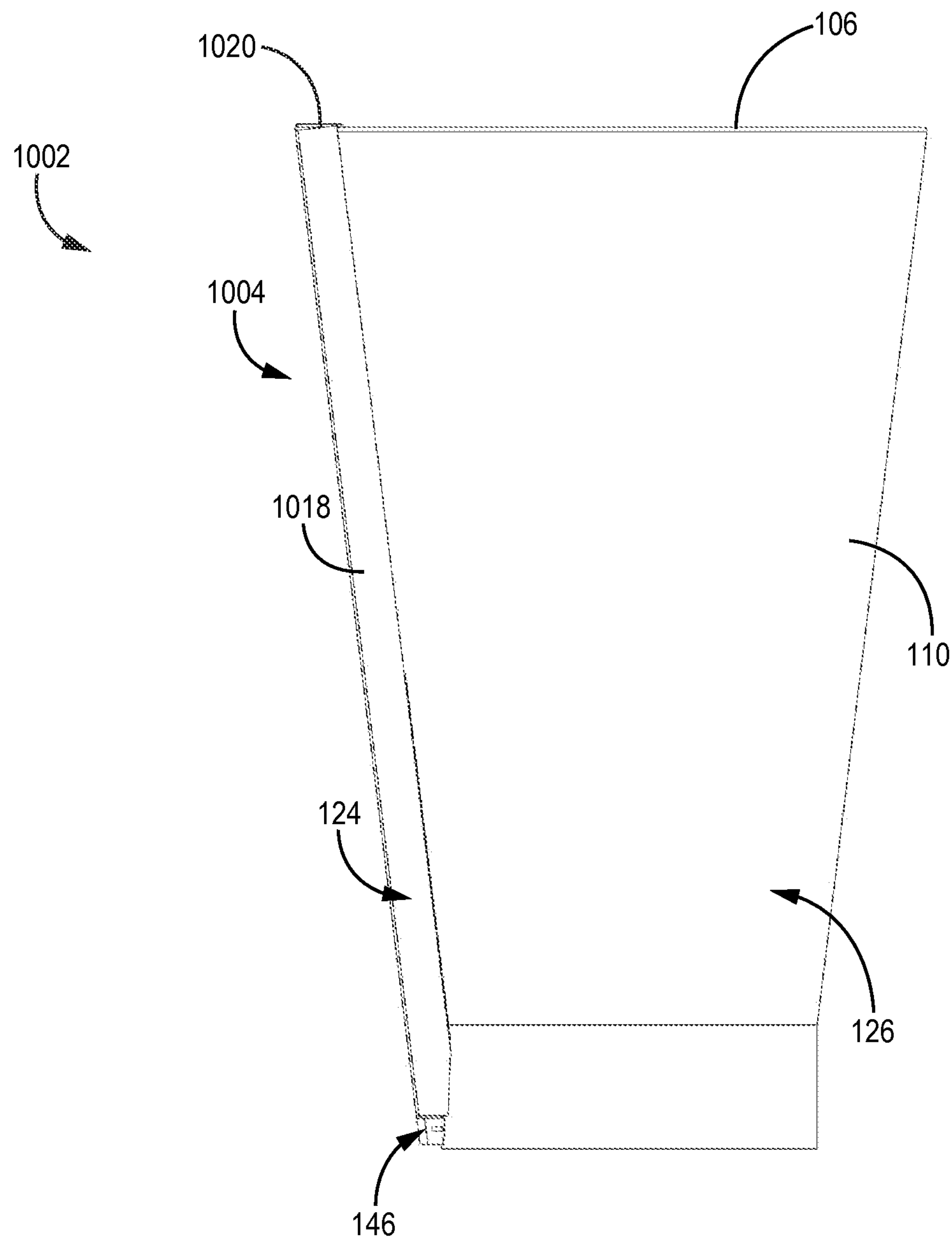
FIG. 10B is a side view of an exemplary embodiment of the container portion of FIG. 10A.
Figure 10C:
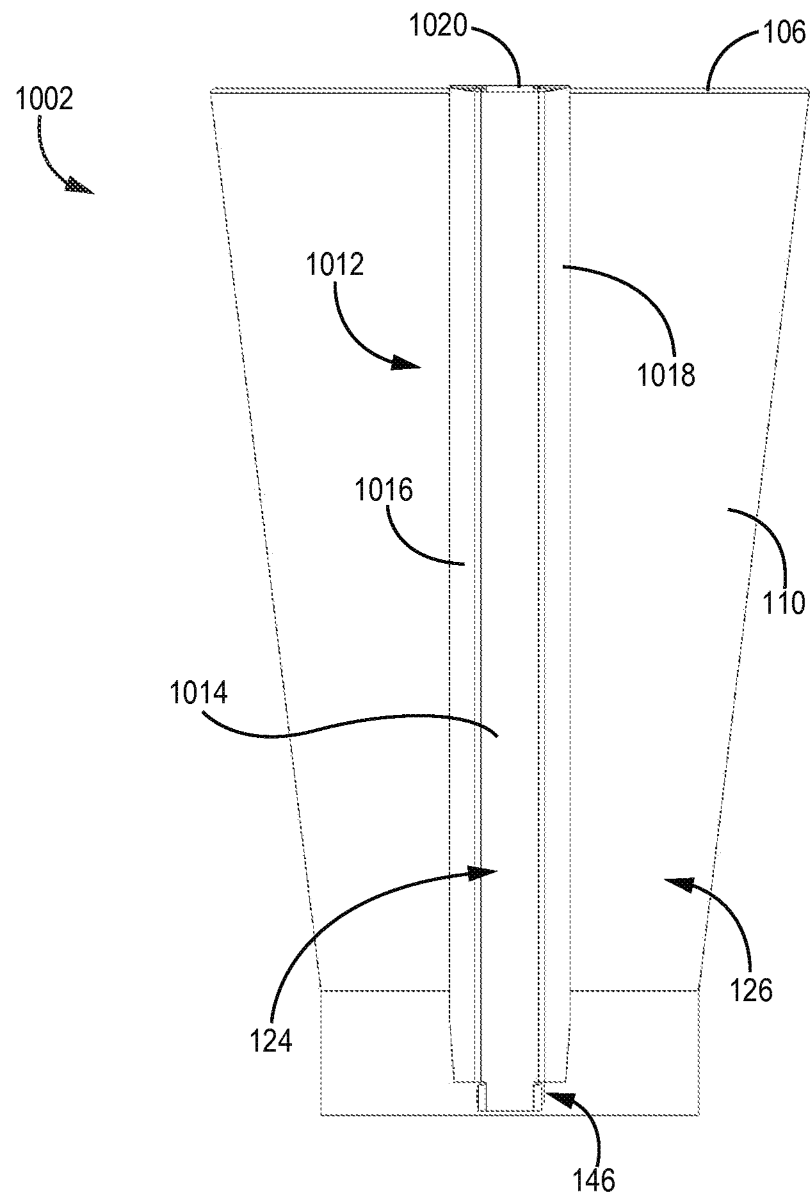
FIG. 10C is another side view of the exemplary embodiment of the container portion of FIG. 10A.
Figure 10D:
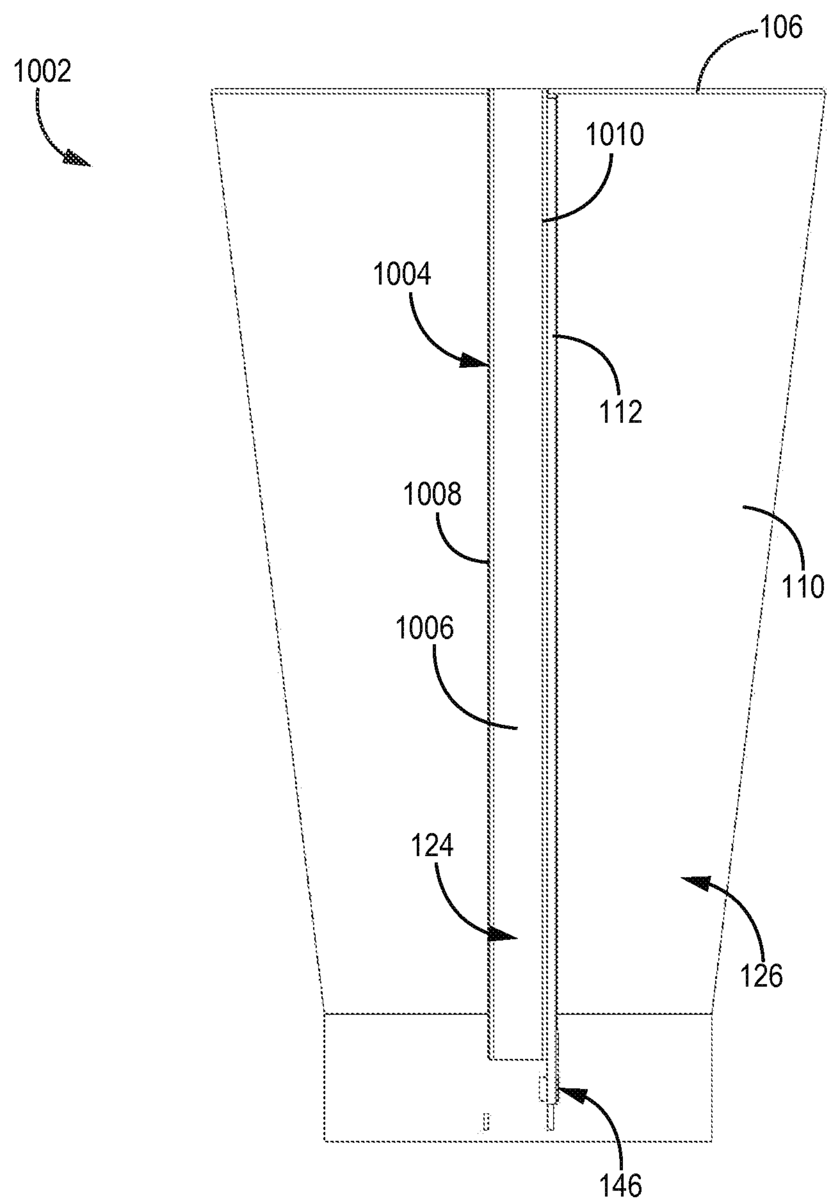
FIG. 10D is another side view of the exemplary embodiment of the container portion of FIG. 10A without the exterior shield so that the capacitive sensor, grounding plane, and voids between the outer notched portion and the main portion of the container portion can be seen.
Figure 10E:
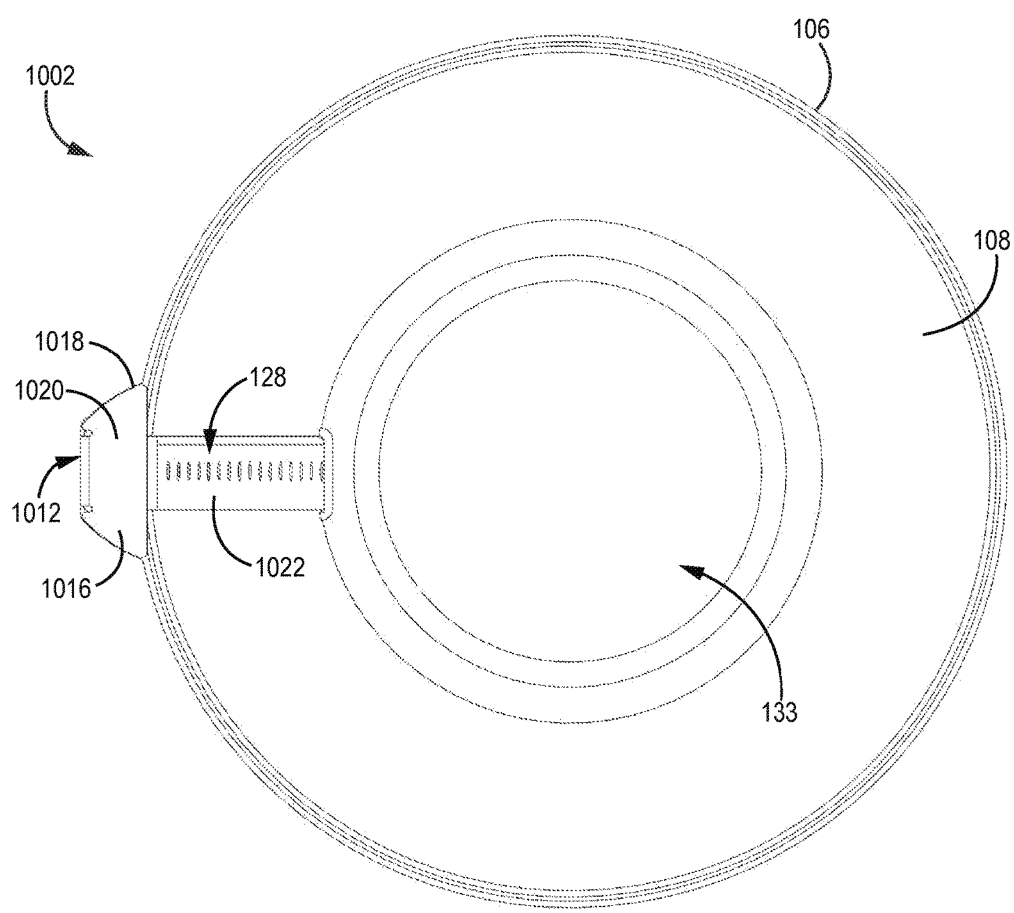
FIG. 10E is a top view of an exemplary embodiment of the container portion of FIG. 10A.
Figure 10F:
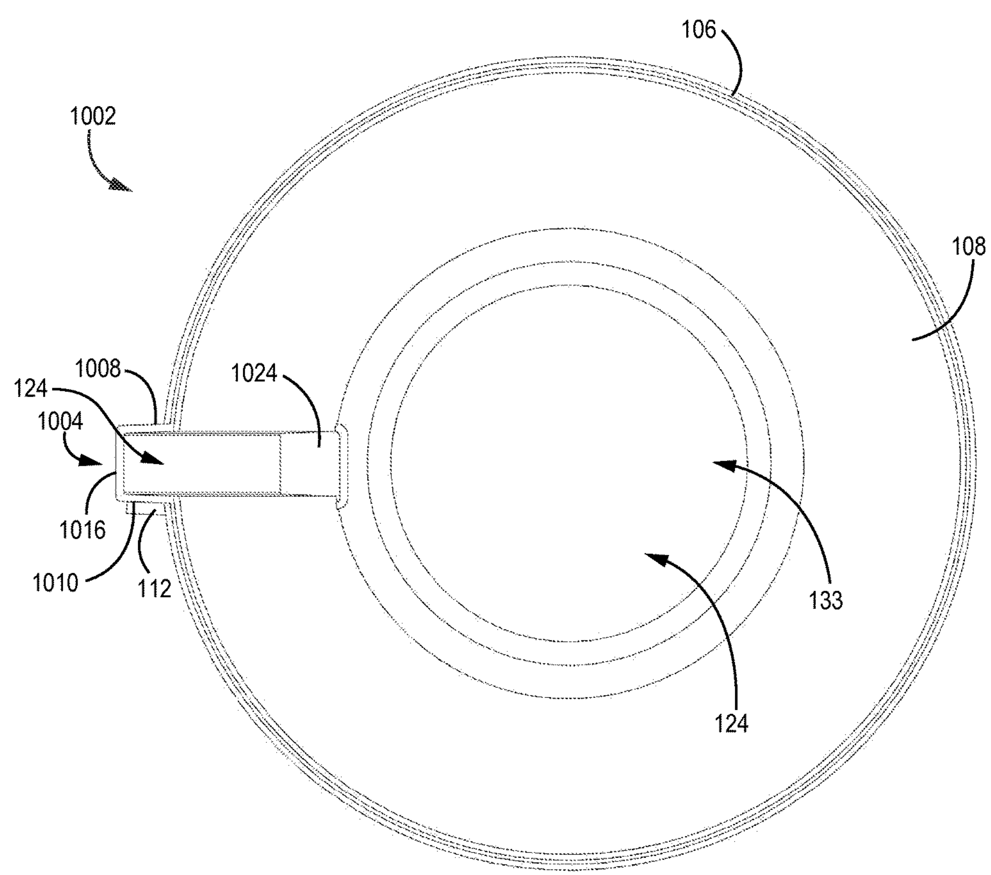
FIG. 10F is another top view of the exemplary embodiment of the container portion of FIG. 10A without the exterior shield so that the capacitive sensor, grounding plane, and voids between the outer notched portion and the main portion of the container portion can be seen.
Figure 10G:
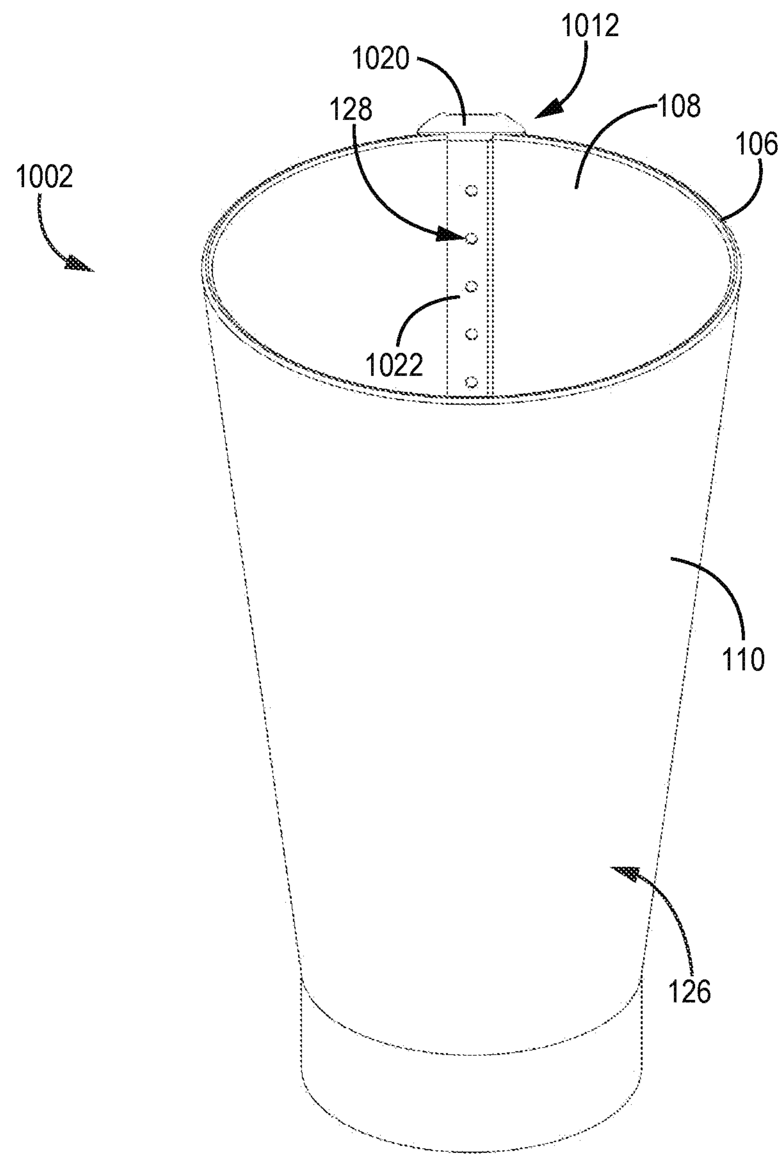
FIG. 10G is another top perspective view of the container portion of FIG. 10A.
Figure 10H:
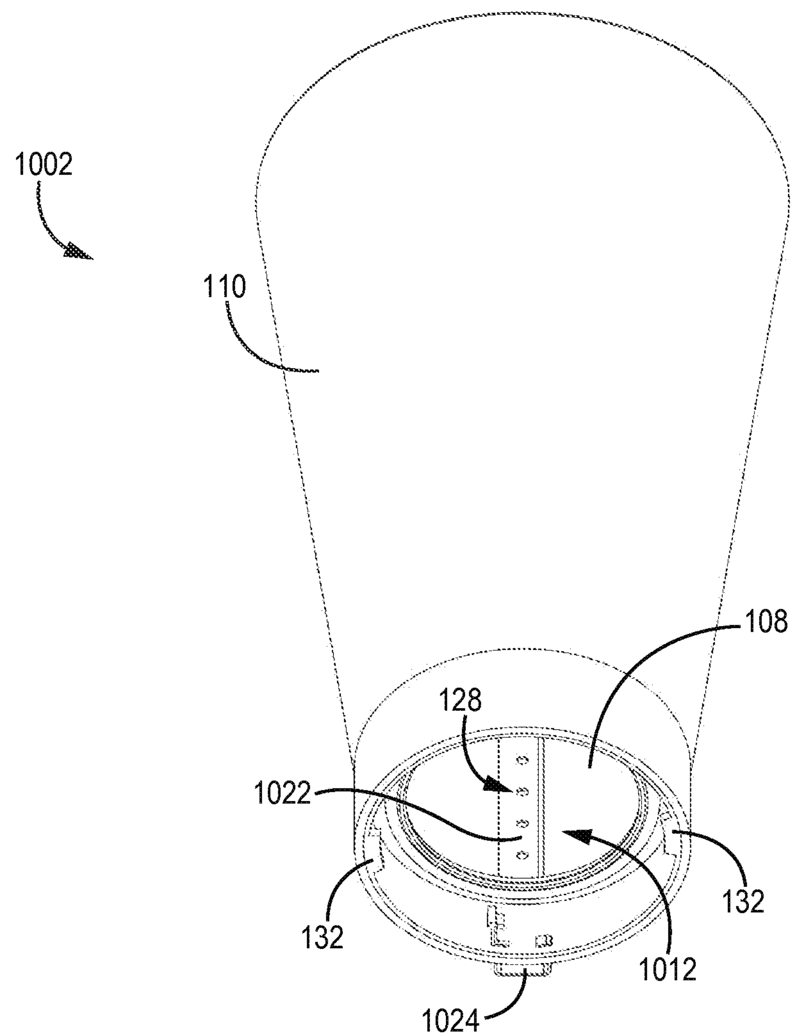
FIG. 10H is bottom perspective view of the container portion of FIG. 10A from the bottom.

FIGS. 10A-10H show different views of another exemplary embodiment of the container portion 102 of the urine measurement device 100, hereinafter container portion 1002. FIG. 10A is a top perspective view of the container portion 1002, FIG. 10B is a side view of the container portion 1002, FIG. 10C is a side view of the container potion 1002 rotated 90 degrees from FIGS. 10A and 10B, FIG. 10D is a side view of the container portion 1002 of FIG. 10C without the at least one shield 1012 such that the notch section 1004 can be seen, FIG. 10E is a top view of the container portion 1002, FIG. 10F is a bottom view of the container portion 1002, FIG. 10G is a top perspective view of the container portion 1002 rotated 90 degrees from FIG. 10A, and FIG. 10H is a bottom perspective view of the container portion 102. The description below focuses on features shown in FIGS. 10A-10H that are distinct from the features of container portion 1002 that are similar to those in contain portion 102.

The primary difference between the container portion 1002 and the container portion 102 described above is that the sensing portion 126 of the container portion is contained in a notch section 1004 that protrudes from the exterior of the main body of the container portion 1002 that includes the non-sensing portion 126. In exemplary embodiments, gap/channel/void/aperture 128 between the notch section 1004 and the main body of the container portion 1002 allow urine, other fluid, and/or other substance to pass from the non-sensing portion 126 where the urine, other fluid, or other substance enter into the container portion 1002 and into the sensing portion 124 in a controlled manner. As with the container portion 102, by only allowing a controlled flow of the urine, other liquid, or other substance into the sensing portion 124, disturbances, turbulence, and/or slosh in the urine, other liquid, or other substance within the non-sensing portion 126 are reduced within the sensing portion 124 of the notch section 1004 of the container portion 1002. As the urine, other fluid, or other substance enters the container portion 1002, it first enters the non-sensing portion 126 and a portion of the urine, other fluid, or other substance enters the sensing portion 124 in a controlled manner through the at least one gap/channel/void/aperture 128. Accordingly, the notch section 1004 acts as a "low-pass" filter for the flow data by protecting the capacitive sensor 112 (or other sensor or sensing element) from the disturbances, turbulence, and slosh of the urine, other fluid, or other substance within the non-sensing portion 126.

In exemplary embodiments, the notch section 1004 includes a front wall 1006, a side wall 1008, and a side wall 1010. In exemplary embodiments, the capacitive sensor 112 (or other sensor or sensing element) is attached to the exterior of the side wall 1010. In exemplary embodiments, the container portion 1002 includes a shield 1012 that covers the notch section 1004 and includes a front wall 1014, a side wall 1016, a side wall 1018, a top 1020, and an interior wall 1022 between the notch section 1004 and the main body of the container portion. In exemplary embodiments, the interior wall 1022 includes the at least one gap/channel/void/aperture 128 between the non-sensing portion 126 and the sensing portion 124. In exemplary embodiment, the notch section includes a bottom surface 1024. As with container portion 102, some implementations of container portion 1002 include a bottom wall 133 while others do not and rely on the top surface 142 of the electronics portion 102 when it is coupled with the container portion 1002 to serve as the bottom wall of the container portion 1002. In exemplary embodiments, the side wall 1008 serves as the grounding plane for the at least one capacitive sensor 112 such that the capacitance measurement is taken across the sensing portion 124 in between the at least one capacitive sensor 112 and the grounding plane.

Figure 11:
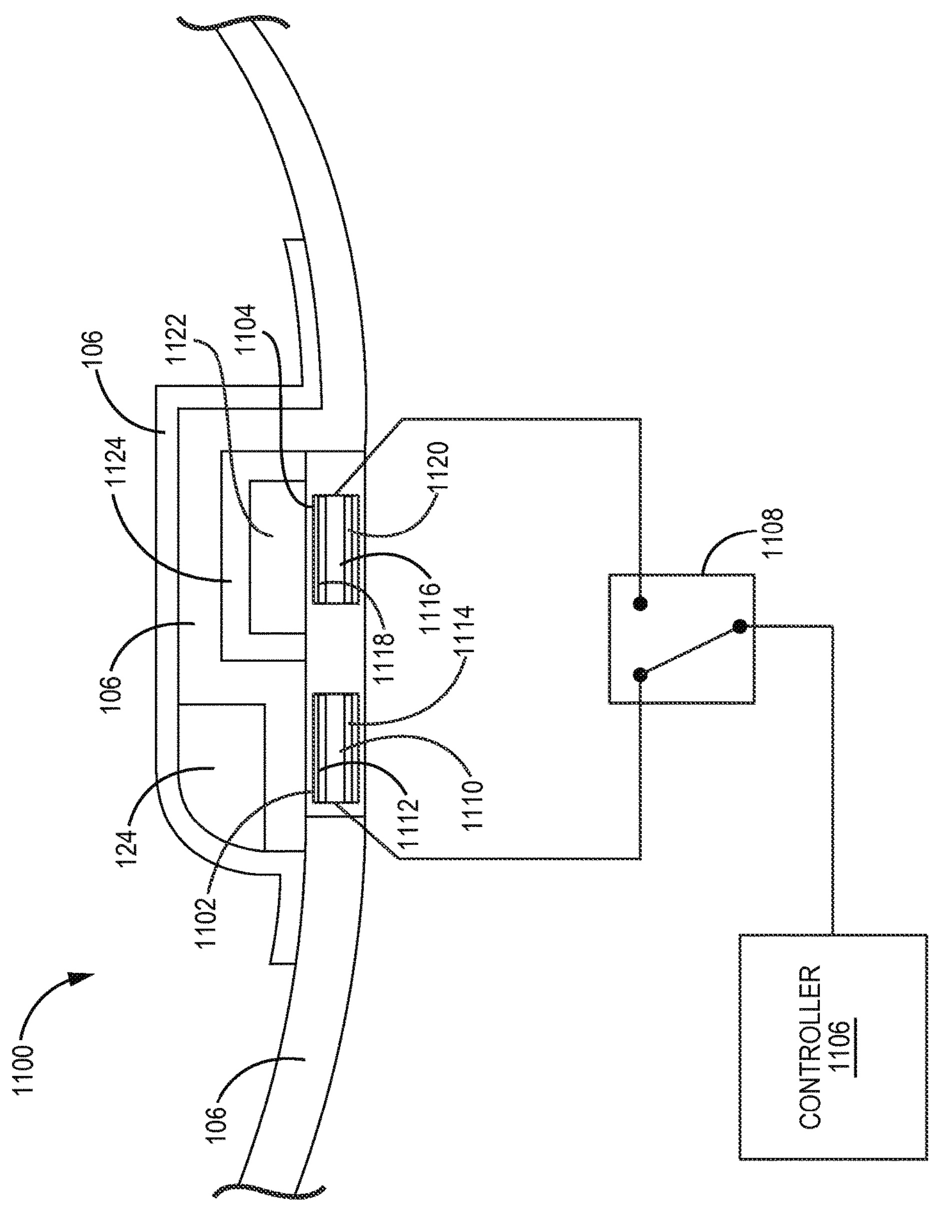
FIG. 11 is a block diagram of an exemplary embodiment of a calibration architecture for calibrating a urine measurement device using capacitive sensors.

FIG. 11 is block diagram of an exemplary embodiment of a calibration architecture 1100 for calibrating a urine measurement device using two capacitive sensors. This calibration architecture 1100 is an exemplary embodiment of an architecture that makes calibration of the sensor for a current environment even simpler than the user driven calibration described above. The calibration architecture 1100 includes a primary capacitive sensor 1102, a secondary capacitive sensor 1104, a controller 1106, and a relay/multiplexer/switch 1108. In exemplary embodiments, both the primary capacitive sensor 1102 and the secondary capacitive sensor 1104 are embodiments of the capacitive sensor 112 described above.

Specifically, the primary capacitive sensor 1102 includes a substrate 1110 having a first capacitive plate 1112 (acting as a sensor electrode facing the measurement volume inside of the container portion 102) on a first side of the substrate 1110 and a second capacitive plate 1114 (acting as a reference electrode to get a reference measurement outside the container portion 102) on a second side of the substrate 1110 opposite the first side of the substrate 1110, such that the substrate 1110 is sandwiched between the first capacitive plate 1112 and the second capacitive plate 1114. In exemplary embodiments, the substrate 1110 is made of a non-conductive material while each of first capacitive plate 1112 and second capacitive plate 1114 are made of conductive material such as aluminum, gold, copper, or an alloy of conductive materials.

Similarly, the secondary capacitive sensor 1104 includes a substrate 1116 having a first capacitive plate 1118 (acting as a sensor electrode facing the measurement volume inside of the container portion 102) on a first side of the substrate 1116 and a second capacitive plate 1120 (acting as a reference electrode to get a reference measurement outside the container portion 102) on a second side of the substrate 1116 opposite the first side of the substrate 1118, such that the substrate 1116 is sandwiched between the first capacitive plate 1118 and the second capacitive plate 1120. In exemplary embodiments, the substrate 1116 is made of a non-conductive material while each of first capacitive plate 1118 and second capacitive plate 1118 are made of conductive material such as aluminum, gold, copper, or an alloy of conductive materials.

In exemplary embodiment, the primary capacitive sensor 1102 and the secondary capacitive sensor 1104 are substantially equivalent in their properties. In exemplary embodiments, the primary capacitive sensor 1102 is used to both (1) take the initial zero percent urine, other fluid, and/or other substance height calibration reading when the container portion 102 is empty; and (2) collect the flow data in real-time during a measurement. In exemplary embodiments, the secondary capacitive sensor 1104 is only used to take the 100 percent urine, other fluid, and/or other substance height calibration reading. The main difference between the primary capacitive sensor 1102 and the second capacitive sensor 1104 is that the secondary capacitive sensor 1104 is configured with a dielectric spacer 1122 with a conductive substrate 1124 opposite the first capacitive plate 1118 of the secondary capacitive sensor 1104. In exemplary embodiments, the first capacitive plate 1118 of the secondary capacitive sensor 1104 is positioned in contact with the dielectric spacer 1122 on one side of the dielectric spacer 1122 and the conductive substrate 1124 is positioned in contact with the other side of the dielectric spacer 1122 opposite the first capacitive plate 1118. In exemplary embodiments, the conductive substrate 1112 is substantially the same height as the secondary capacitive sensor 1104 and synthesizes the height at which the container would be 100 percent full.

In exemplary embodiments, the calibration architecture 1100 is integrated into or placed on the outside surface 110 of the side-wall 106 of an embodiment of the container portion 102. In exemplary embodiments, both all of the primary capacitive sensor 1102, the secondary capacitive sensor 1104, the dielectric spacer 1122, and the conductive substrate 1124 are outside of the side-wall 106. In exemplary embodiments, the sensing portion 124 is created inside of the interior shield 122. In exemplary embodiments, the primary capacitive sensor 1102 and the second capacitive sensor 1104 are on a single printed circuit board. In other embodiments, primary capacitive sensor 1102 and the secondary capacitive sensor 1104 are on separate printed circuit boards.

In exemplary embodiments, the relay/multiplexer/switch 1108 is used to allow the controller 1106 to: (1) first sample the primary capacitive sensor 1102 while the container portion 102 is empty to get the zero percent full calibration point in the current environment; (2) toggle to the secondary capacitive sensor 1104 to collect a synthesized 100 percent full calibration point based on the dielectric spacer 1122 and the conductive substrate 1124 simulating a 100 percent full calibration point in the current environment; and (3) toggles back to the primary capacitive sensor 1102, ready for the urination voiding event and calibrated to the current environment. In exemplary embodiments, the indicator 148 (such as an LED) indicates that the calibration event has ended and that the device is ready for measurement of a urination voiding event.

In exemplary embodiments, the conductive substrate 1124 is replaced with an internally contained column of water that is also grounded. The internally contained column of water is held in a water tight enclosure to give it the shape and surface area which a sheet of conductive material would have.

Figure 12:
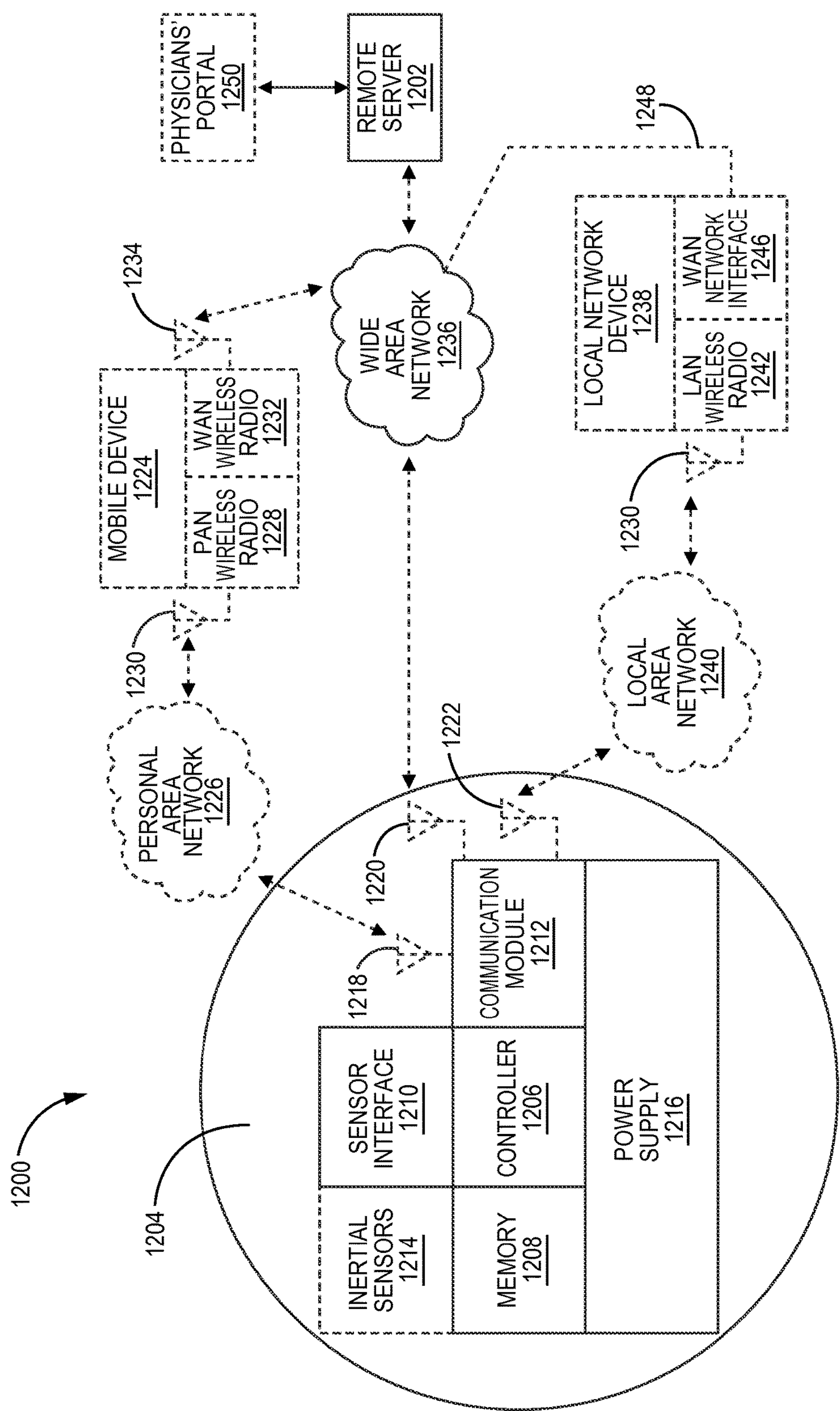
FIG. 12 is a block diagram of an exemplary system including the urine measurement device of FIG. 1A In accordance with common practice, the various described features are not drawn to scale but are drawn to emphasize specific features relevant to the exemplary embodiments. Like reference numbers and designations in the various drawings indicate like elements.

FIG. 12 is a block diagram of an exemplary system 1200 enabling transmission of data from a urine measurement device (such as urine measurement device 100) to a remote server 1202. In exemplary embodiments, an electronics portion 1204 (such as electronics portion 104 or electronics portion 804) of a urine measurement device is communicatively coupled with a remote server 1202 in various ways. In exemplary embodiments, the electronics portion 1204 includes a controller 1206, memory 1208, at least one sensor interface 1210, at least one communication module 1212, optional inertial sensors 1214, and a power supply 1216. In exemplary embodiments, the power supply provides power to the controller 1206, memory 1208, the at least one sensor interface 1210, the at least one communication module 1212, and the optional inertial sensors 1214.

In exemplary embodiments, the controller 1206 implements at least some of the processing described herein. In exemplary embodiments, the controller 1206 is a programmable processor, such as a microcontroller, an application-specific integrated circuit (ASIC), a field-programmable gate array (FPGA), a field-programmable object array (FPOA), or a programmable logic device (PLD). The controller 1206 described above may include or function with software programs, firmware or other computer readable instructions for carrying out various methods, process tasks, calculations, and control functions, described herein. These instructions are typically stored on any appropriate computer readable medium used for storage of computer readable instructions or data structures. The computer readable medium can be implemented as any available media that can be accessed by a general purpose or special purpose computer or processor, or any programmable logic device. Suitable processor-readable media may include storage or memory media such as magnetic or optical media. For example, storage or memory media may include conventional hard disks, Compact Disk-Read Only Memory (CD-ROM), volatile or non-volatile media such as Random Access Memory (RAM) (including, but not limited to, Synchronous Dynamic Random Access Memory (SDRAM), Double Data Rate (DDR) RAM, RAMBUS Dynamic RAM (RDRAM), Static RAM (SRAM), etc.), Read Only Memory (ROM), Electrically Erasable Programmable ROM (EEPROM), and flash memory, etc. Suitable processor-readable media may also include transmission media such as electrical, electromagnetic, or digital signals, conveyed via a communication medium such as a network and/or a wireless link.

In exemplary embodiments, the at least one sensor interface 1210 is configured to interface with the capacitive sensor 112 (or other sensor or sensing device) of the container portion and any additional at least one sensor 806 present in the urine measurement device. In exemplary embodiments, the controller 1206 is configured to measure or calculate at least one of flow rate; urine, other fluid, and/or other substance height and volume based on the signals received at the at least one sensor interface 1210 from the at least one capacitive sensor 112. In exemplary embodiments, the raw voltage value read from the sensors; the calculated flow rate; urine, other fluid, and/or other substance height and/or volume is saved in the memory 1208 or on another storage device. In exemplary embodiments, the raw voltage value read from the sensors, the calculated flow rate and/or urine, other fluid, and/or other substance height and/or volume is associated with a counter and/or time. In exemplary embodiments, the raw voltage value read from the sensors, the calculated flow rate and/or urine, other fluid, and/or another substance height and/or volume is transmitted to an external device using the at least one communication module 1212. In exemplary embodiments, the at least one communication module 1212 includes at least one processor as described herein, at least one radio, and/or at least one wired network interface. In other exemplary embodiments, the controller 1206 is configured to take measurements of voltage that correspond to a capacitance from the capacitive sensor 112 through the at least one sensor interface 1210 and to save the measurement in the memory 1208 or on another storage device. In exemplary embodiments, the capacitance measurements are associated with a counter and/or time. In exemplary embodiments, the capacitance measurements or raw voltage values are transmitted to an external device using the at least one communication module 1212. In exemplary embodiments data collected form the additional at least one sensor 806 is stored in the memory 1208 or another storage device and/or transmitted to an external device using the at least one communication module 1212.

In exemplary embodiments, the optional inertial sensors 1214 are configured to provide inertial measurement data to the controller 1206 that is used to compensate for any tilt of the container portion 102 during measurement of the flow rate and/or urine, other fluid, and/or other substance height and/or volume. In exemplary embodiments, the optional inertial sensors include at least one accelerometer and/or at least one gyroscopes configured to measure tilt in particular directions and/or rotation around particular axes. In exemplary embodiments, the controller 1206 compensates the data for any tilt and/or vertical perturbations detected by the optional inertial sensors 1214 (such as an accelerometers detecting vertical error and/or gyroscopes detecting rotation/tilt) which could lead to false volumetric measurement if not mitigated. In other embodiments, the data from the inertial sensors is included with the data regarding the flow rate and/or urine, other fluid, and/or other substance height and/or volume that is provided to an external device for processing, such as the mobile device 1224, local network device 1238, and/or remote server 1202 described herein and the external device performs the compensation of the data for any tilt and/or vertical perturbations detected by the optional inertial sensors 1214 (such as an accelerometers detecting vertical error and/or gyroscopes detecting rotation/tilt) which could lead to false volumetric measurement if not mitigated. In exemplary embodiments, the data from the optional inertial sensors is used to compensate tilt in combination with a plurality of capacitive sensors 112 (such as capacitive sensors 612A, 612B, and 612C of FIG. 6 described above) and/or the stabilizing handle portion 902 of FIG. 9 described above.

In exemplary embodiments, data provided by the optional inertial sensors 1214 is used to validate that the bottom of the container portion 102 is parallel to the ground, but is not used to actually compensate for the container portion 102 not being parallel to the ground. Instead, in exemplary embodiments when the data from the optional inertial sensors 1214 indicates that the bottom of the container portion 102 is not parallel to the ground, an alert is provided to the user (such as through the indicator 148), so that the user can attempt to correct the issue. In addition, in exemplary embodiments when the data from the optional inertial sensor 1214 indicates that the bottom of the container portion 102 is not parallel to the ground, a flag can be included in the measurement file to indicate that the device was not level during operation.

FIG. 12 shows three distinct data paths from the electronics portion 1204 to the remote server 1202, though additional paths are possible. In exemplary embodiments, the at least one communication module 1212 includes a separate antenna for each data path, such as antenna 1218, antenna 1220, and antenna 1222. In exemplary embodiments, the at least one communication module 1212 communicates data to a mobile device 1224 through a personal area network 1226, such as a Bluetooth connection. In exemplary embodiments, the mobile device 1224 includes a personal area network (PAN) wireless radio 1228 having an antenna 1230 and a wide area network (WAN) radio 1232 having an antenna 1234. In exemplary embodiments, at least one communication module 1212 of the electronics portion 1204 communicates signals via the antenna 1218 across the personal area network 1226 to the PAN wireless radio 1228 of the mobile device 1224 via the antenna 1230. In exemplary embodiments, the mobile device 1224 includes a processor that performs processing of the data received from the electronics portion 1204. In exemplary embodiments, the mobile device 1224 communicates data across a wide area network 1236 to the remote server using WAN wireless radio 1232 via antenna 1234.

In exemplary embodiments, the at least one communication module 1212 communicates data to the remote server 1202 across the wide area network 1236 using antenna 1220. In exemplary embodiments, the at least one communication module 1212 includes a cellular data modem and the wide area network 1236 is implemented at least in part using a cellular data communication network.

In exemplary embodiments, the at least one communication module 1212 communicates data to a local network device 1238 across the local area network 1240, such as a WiFi network, using antenna 1222. In exemplary embodiments, the local network device 1238 includes a local area network (LAN) wireless radio 1242 having an antenna 1244 and a wide area network (WAN) network interface 1246 communicatively coupled to the wide area network 1236 by a communication link 1248. In exemplary embodiments, the at least one communication module 1212 of the electronics portion 1204 communicates signals via the antenna 1218 across the local area network 1240 to the LAN wireless radio 1242 via the antenna 1244. In exemplary embodiments, the local network device 1238 includes a processor that performs processing of the data received form the electronics portion 1204. In exemplary embodiments, the local network device 1238 communicates data across a wide area network 1236 via the communication link 1248 to the remote server 1202.

In exemplary embodiments, the communication link 1248 is at least in part across a wired communication medium. In other exemplary embodiments, the communication link 1248 is at least in part across a wireless communication medium. While wireless and/or wired communication elements are described herein, it is understood that other embodiments may include different types of communication in different areas of the system 1200.

In exemplary embodiments, the electronics within the electronics portion 1204, and specifically the controller 1206, can be updated through over-the-air (OTA) firmware and/or software updates. In exemplary embodiments, the data collected at the remote server 1202 can be accessed remotely by physicians, other health providers, and others using a physicians' portal 1250. In exemplary embodiments, at least one of the controller 1206, the mobile device 1124, the local network device 1238, the remote server 1202, the physicians' portal 1250, and/or another device generates a voiding diary and/or other reports which can track various properties of urine over time including but not limited volume, flow rate, glucose, blood, bacteria, color, odor, turbidity, specific gravity, pH, protein, ketones, urobilinogen, bilirubin, nitrite and leukocytes.

EXAMPLE EMBODIMENTS

Example 1 includes a substance measurement device, comprising: a container portion configured to receive a substance; a sensing device configured to measure a property of the substance related to at least one of a flow rate of the substance into the container portion, a level of the substance within the container portion, and a volume of the substance within the container portion; and at least one shield positioned within the container portion and configured to provide at least one of: a mechanical buffer between the substance entering the container portion and the sensing device; and an electrical shield between the substance entering the container portion and the sensing device.

Example 2 includes the substance measurement device of Example 1, wherein the substance is a liquid.

Example 3 includes the substance measurement device of any of Examples 1-2, wherein the substance is urine.

Example 4 includes the substance measurement device of any of Examples 1-3, wherein the first sensing device is a capacitive sensor.

Example 5 includes the substance measurement device of Example 4, further comprising: a controller communicatively coupled to the first sensing device and configured to perform at least one of: capture raw data indicative of capacitance from the capacitive sensor and store it in at least one of a memory and a storage device; and calculate at least one of the flow rate of the substance into the container portion, the level of the substance within the container portion, and the volume of the substance within the container portion based on raw data from the capacitive sensor over time.

Example 6 includes the substance measurement device of Example 5, further comprising: an electronics portion removably coupled with the container portion, wherein the electronics portion includes the controller.

Example 7 includes the substance measurement device of Example 6, wherein the electronics portion further includes: a communication module communicatively coupled to the controller.

Example 8 includes the substance measurement device of any of Examples 1-7, wherein the at least one shield partitions a sensing portion of the container portion from a non-sensing portion of the container portion; wherein the non-sensing portion of the container portion is configured to receive the substance from outside of the container portion; wherein sensing portion of the container portion is configured to receive the substance from the non-sensing portion of the container portion through at least one of gaps, channels, and voids below, around, or through the at least one shield; and wherein the sensing device is configured to measure the property of the substance within the sensing portion of the container portion.

Example 9 includes the substance measurement device of any of Examples 1-8, further comprising: an exterior shield positioned on the outside of the container portion and configured to isolate the sensing device from external disturbances caused by effects of an external environment outside of the container portion.

Example 10 includes the substance measurement device of any of Examples 1-9, wherein the container portion includes at least one tapered side-wall that tapers from a smaller size at a lower portion of the container portion to a larger size at an upper portion of the container portion above the lower portion of the container portion.

Example 11 includes the substance measurement device of any of Examples 1-10, further comprising: an electronics portion removably coupled with the container portion; wherein the container portion does not include a bottom wall; wherein a top surface of the electronics portion serves as a bottom for the container portion when the electronics portion is coupled with the container portion.

Example 12 includes the substance measurement device of Example 11, wherein the top surface of the electronics portion includes additional sensors that come into contact with the substance when it enters the container portion.

Example 13 includes the substance measurement device of any of Examples 1-10, wherein the container portion includes at least one side-wall and a bottom wall.

Example 14 includes the substance measurement device of any of Examples 1-13, further comprising: an electronics portion removably coupled with the container portion using complimentary coupling elements.

Example 15 includes the substance measurement device of Example 14, wherein the complimentary coupling elements include at least one of threads, bayonet mounts, tabs, clips, and fasteners.

Example 16 includes a liquid measurement device, comprising: a liquid collection container portion configured to receive liquid; a capacitive sensor configured to measure changes in capacitance within the liquid collection container portion due to changes in the level of the within the liquid collector container portion; a controller communicatively coupled to the capacitive sensor; at least one shield positioned within the container portion and configured to provide both: a mechanical buffer between the liquid entering the container portion and the sensing device; and an electrical shield between the liquid entering the container portion and the sensing device; and wherein the controller is configured to perform at least one of: capture raw data indicative of capacitance from the capacitive sensor and store it in at least one of a memory and a storage device; and calculate at least one of the flow rate of the urine into the container portion, the level of the urine within the container portion, and the volume of the urine within the container portion based on raw data from the capacitive sensor over time.

Example 17 includes the liquid measurement device of Example 16, further comprising: an electronics portion removably coupled with the liquid collection container portion, wherein the electronics portion includes the controller and a communication module communicatively coupled to the controller.

Example 18 includes the liquid measurement device of any of Examples 16-17, further comprising: an electronics portion removably coupled with the liquid collection container portion; wherein the liquid collection container portion does not include a bottom wall; wherein a top surface of the electronics portion serves as a bottom for the liquid collection container portion when the electronics portion is coupled with the liquid collection container portion.

Example 19 includes a urine measurement device, comprising: a urine collection container portion configured to receive urine; a capacitive sensor configured to measure changes capacitance within the urine collection container portion due to changes in the level of the urine within the urine collection container portion; a controller communicatively coupled to the capacitive sensor; at least one shield positioned within the container portion and configured to provide both: a mechanical buffer between the urine entering the container portion and the sensing device; and an electrical shield between the urine entering the container portion and the sensing device; at least one exterior shield positioned on the outside of the urine collection container portion and configured to isolate the capacitive sensor from external disturbances caused by effects of an external environment outside of the urine collection container portion; and wherein the controller is configured to perform at least one of: capture raw data indicative of capacitance from the capacitive sensor and store it in at least one of a memory and a storage device; and calculate at least one of the flow rate of the urine into the container portion, the level of the urine within the container portion, and the volume of the urine within the container portion based on raw data from the capacitive sensor over time.

Example 20 includes the urine measurement device of Example 19, further comprising: an electronics portion removably coupled with the liquid collection container portion using complimentary coupling elements, wherein the electronics portion includes the controller and a communication module communicatively coupled to the controller; wherein the liquid collection container portion does not include a bottom wall; wherein a top surface of the electronics portion serves as a bottom for the liquid collection container portion when the electronics portion is coupled with the liquid collection container portion.

Although specific embodiments have been illustrated and described herein, it will be appreciated by those of ordinary skill in the art that any arrangement, which is calculated to achieve the same purpose, may be substituted for the specific embodiments shown. Therefore, it is manifestly intended that this invention be limited only by the claims and the equivalents thereof.

What is claimed is:

1. A substance measurement device, comprising:

a container portion having a sensing portion and a non-sensing portion, the non-sensing portion of the container portion configured to receive a substance from outside of the container portion;

at least one sensor positioned within the sensing portion of the container portion, the at least one sensor configured for a measurement of a property of the substance within the sensing portion of the container portion, the property related to at least one of a flow rate of the substance into the container portion, a level of the substance within the container portion, or a volume of the substance within the container portion; and at least one shield positioned within the container portion between the sensing portion and the non-sensing portion, the sensing portion of the container portion configured to receive the substance from the non-sensing portion of the container portion through a plurality of paths, each of the plurality of paths including a gap, channel, void, or aperture below, around, or through the at least one shield, the at least one shield configured to provide at least one of:

buffering between the substance entering the non-sensing portion of the container portion and the at least one sensor positioned within the sensing portion of the container portion by controlling flow of the substance from the non-sensing portion of the container portion to the sensing portion of the container portion; or shielding between the substance entering the non-sensing portion of the container portion and the at least one sensor positioned within the sensing portion of the container portion to block the at least one sensor from sensing outside of the sensing portion of the container portion.

2. The substance measurement device of claim 1, wherein the substance is a liquid.

3. The substance measurement device of claim 1, wherein the substance is urine.

4. The substance measurement device of claim 1, wherein the at least one sensor includes a capacitive sensor.

5. The substance measurement device of claim 4, further comprising:

a controller communicatively coupled to the at least one sensor and configured to perform at least one of:

capture raw data indicative of capacitance from the capacitive sensor and store it in at least one of a memory and a storage device; or calculate at least one of the flow rate of the substance into the container portion, the level of the substance within the container portion, and the volume of the substance within the container portion based on raw data from the capacitive sensor over time.

6. The substance measurement device of claim 5, further comprising:

an electronics portion removably coupled with the container portion, wherein the electronics portion includes the controller.

7. The substance measurement device of claim 6, wherein the electronics portion further includes:

a communication module communicatively coupled to the controller.

8. The substance measurement device of claim 1, further comprising:

an exterior shield positioned on the outside of the container portion and configured to isolate the at least one sensor from external disturbances caused by effects of an external environment outside of the container portion.

9. The substance measurement device of claim 1, wherein the container portion includes at least one tapered side-wall that tapers from a smaller size at a lower portion of the container portion to a larger size at an upper portion of the container portion above the lower portion of the container portion.

10. The substance measurement device of claim 1, further comprising:

an electronics portion removably coupled with the container portion;

wherein the container portion does not include a bottom wall;

wherein a top surface of the electronics portion serves as a bottom for the container portion when the electronics portion is coupled with the container portion.

11. The substance measurement device of claim 10, wherein the top surface of the electronics portion includes additional sensors that come into contact with the substance when it enters the container portion.

12. The substance measurement device of claim 1, wherein the container portion includes at least one side-wall and a bottom wall.

13. The substance measurement device of claim 1, further comprising:

an electronics portion removably coupled with the container portion using complimentary coupling elements.

14. The substance measurement device of claim 13, wherein the complimentary coupling elements include at least one of threads, bayonet mounts, tabs, clips, or fasteners.

15. The substance measurement device of claim 1, wherein the at least one shield is configured to provide:

buffering between the substance entering the non-sensing portion of the container portion and the at least one sensor positioned within the sensing portion of the container portion by controlling flow of the substance from the non-sensing portion of the container portion to the sensing portion of the container portion.

16. The substance measurement device of claim 1, wherein controlling flow of the substance from the non-sensing portion of the container portion to the sensing portion of the container portion includes reducing disturbances, turbulence, or slosh of the substance entering the non-sensing portion of the container portion from being transferred to the sensing portion of the container portion, wherein the disturbances, turbulence, or slosh affect measurement of the property by the at least one sensor positioned within the sensing portion of the container portion, wherein the at least one shield and the plurality of paths act as a mechanical low-pass filter for the measurement of the property by the at least one sensor positioned within the sensing portion of the container portion.

17. A liquid measurement device, comprising:

a container portion having a sensing portion and a non-sensing portion, the non-sensing portion of the container portion configured to receive liquid from outside of the container portion;

a capacitive sensor positioned within the sensing portion of the container portion, the capacitive sensor configured for a measurement of changes in capacitance within the sensing portion of the container portion due to changes in the level of the liquid within the container portion; and a controller communicatively coupled to the capacitive sensor;

at least one shield positioned within the container portion between the sensing portion and the non-sensing portion, the sensing portion of the container portion configured to receive the liquid from the non-sensing portion of the container portion through a plurality of paths, each of the plurality of paths including a gap, channel, void, or aperture below, around, or through the at least one shield, the at least one shield configured to provide at least one of:

buffering between the liquid entering the non-sensing portion of the container portion and the capacitive sensor positioned within the sensing portion of the container portion by controlling flow of the liquid from the non-sensing portion of the container portion to the sensing portion of the container portion; or shielding between the liquid entering the non-sensing portion of the container portion and the capacitive sensor positioned within the sensing portion of the container portion by blocking the capacitive sensor from sensing outside of the sensing portion of the container portion; and wherein the controller is configured to perform at least one of:

capture raw data indicative of capacitance from the capacitive sensor and store it in at least one of a memory and a storage device; or calculate at least one of the flow rate of the liquid into the container portion, the level of the liquid within the container portion, and the volume of the liquid within the container portion based on raw data from the capacitive sensor over time.

18. The liquid measurement device of claim 17, further comprising:

an electronics portion removably coupled with the container portion, wherein the electronics portion includes the controller and a communication module communicatively coupled to the controller.

19. The liquid measurement device of claim 17, further comprising:

an electronics portion removably coupled with the container portion;

wherein the container portion does not include a bottom wall;

wherein a top surface of the electronics portion serves as a bottom for the container portion when the electronics portion is coupled with the container portion.

20. The liquid measurement device of claim 17, wherein the at least one shield is configured to provide:

buffering between the liquid entering the non-sensing portion of the container portion and the capacitive sensor positioned within the sensing portion of the container portion by controlling flow of the liquid from the non-sensing portion of the container portion to the sensing portion of the container portion.

21. The liquid measurement device of claim 17, wherein the liquid is urine.

22. The liquid measurement device of claim 17, wherein controlling flow of the liquid from the non-sensing portion of the container portion to the sensing portion of the container portion includes reducing disturbances, turbulence, or slosh of the liquid entering the non-sensing portion of the container portion from being transferred to the sensing portion of the container portion, wherein the disturbances, turbulence, or slosh affect the measurement of the changes in capacitance by the capacitive sensor positioned within the sensing portion of the container portion, wherein the at least one shield and the plurality of paths act as a mechanical low-pass filter for the measurement of the changes in capacitance by the capacitive sensor positioned within the sensing portion of the container portion.

23. A urine measurement device, comprising:

a container portion having a sensing portion and a non-sensing portion, the non- sensing portion of the container portion configured to receive urine from outside of the container portion;

a capacitive sensor positioned within the sensing portion of the container portion, the capacitive sensor configured for a measurement of changes capacitance within the sensing portion of the container portion due to changes in the level of the urine within the container portion;

at least one shield positioned within the container portion, the sensing portion of the container portion configured to receive the urine from the non-sensing portion of the container portion through a plurality of paths, each of the plurality of paths including a gap, channel, void, or aperture below, around, or through the at least one shield, the at least one shield configured to provide buffering between the urine entering the non-sensing portion of the container portion and the capacitive sensor positioned within the sensing portion of the container portion by controlling flow of the urine from the non-sensing portion of the container portion to the sensing portion of the container portion; and at least one exterior shield positioned on the outside of the container portion and configured to isolate the capacitive sensor from external disturbances caused by effects of an external environment outside of the container portion.

24. The urine measurement device of claim 21, further comprising:

an electronics portion removably coupled with the container portion using complimentary coupling elements, wherein the electronics portion includes the controller and a communication module communicatively coupled to the controller;

wherein the container portion does not include a bottom wall;

wherein a top surface of the electronics portion serves as a bottom for the container portion when the electronics portion is coupled with the container portion.

25. The urine measurement device of claim 23, further comprising:

a controller communicatively coupled to the capacitive sensor, wherein the controller is configured to perform at least one of:

capture raw data indicative of capacitance from the capacitive sensor and store it in at least one of a memory and a storage device; or calculate at least one of the flow rate of the urine into the container portion, the level of the urine within the container portion, and the volume of the urine within the container portion based on raw data from the capacitive sensor over time.

26. The urine measurement device of claim 23, wherein controlling flow of the urine from the non-sensing portion of the container portion to the sensing portion of the container portion includes reducing disturbances, turbulence, or slosh of the urine entering the non-sensing portion of the container portion from being transferred to the sensing portion of the container portion, wherein the disturbances, turbulence, or slosh affect the measurement of the changes in capacitance by the capacitive sensor positioned within the sensing portion of the container portion, wherein the at least one shield and the plurality of paths act as a mechanical low-pass filter for the measurement of the changes in capacitance by the capacitive sensor positioned within the sensing portion of the container portion.

* * * * *